US007449443B2

(12) United States Patent
Tirrell et al.

(10) Patent No.: US 7,449,443 B2
(45) Date of Patent: Nov. 11, 2008

(54) METHOD FOR STABILIZATION OF PROTEINS USING NON-NATURAL AMINO ACIDS

(75) Inventors: David A. Tirrell, Pasadena, CA (US); Yi Tang, San Gabriel, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/851,564

(22) Filed: May 21, 2004

(65) Prior Publication Data

US 2004/0214988 A1 Oct. 28, 2004

Related U.S. Application Data

(63) Continuation of application No. 09/620,691, filed on Jul. 20, 2000, now abandoned.

(60) Provisional application No. 60/191,640, filed on Mar. 23, 2000.

(51) Int. Cl.
C07K 14/00 (2006.01)
C07K 14/39 (2006.01)

(52) U.S. Cl. .......................... 514/2; 530/324; 530/350; 530/371

(58) Field of Classification Search ........................ None
See application file for complete search history.

(56) References Cited

U.S. PATENT DOCUMENTS 4,879,223 A 11/1989 Miyazawa et al. ............ 435/68

OTHER PUBLICATIONS

Huffman et al. 'Substrate Specificity of Isopenicillin N Synthase.' J. Med. Chem. vol. 35, pp. 1897-1914, 1992.*
Berendsen, Herman. "A Glimpse of the Holy Grail?" Science. vol. 282, pp. 642-643.*
Schneider et al. "A Designed Buried Salt Bridge in a Heterodimeric Coiled Coil," J. of Am. Chem. Soc. vol. 119, No. 24: Jun. 18, 1997, pp. 5742-5743.*
Hirst et al. "Predicting leucine zipper structures from sequence," Protein Engineering Desing and Protein, vol. 9, No. 8, pp. 657-662, 1996.*
Nomizu et al. Assembly of Synthetic Laminin Pepties into a Triple-Stranded Coiled Coil Structure. J. of Biol. Chem. vol. 269, No. 48. pp 30386-30392. 1994.*
Bauer et al. Computational approaches to identify Leucine zippers. Nucleic Acid Research, vol. 26, No. 11, pp. 2740-2746. 1998.*
Arai et al., "Synthesis of [Hexafluorovalyl]Gramicidin S", *Bull Chem Soc Jpn.* 1996, 69:1383-89.
Russell et al., *Chem Abstract* 1986, 104:202518b.
Koide et al., "Biosynthesis of Epidermal Growth Factor Having Nonprotein Amino Acid Residue by *Escherichia coli*", Amino Acids: Chem., Biol. Med., [Pap. Int. Congr. Amion Acid Res.] 1990 (Meeting Date 1989), 193-200, Abstract (1992) (An No. 1992:122148).

Aizawa, Y. et al., "Stability of the Dimerization Domain Effects the Cooperative DNA Binding of Short Peptides", *Biochemistry* (1999), 38, 4008-4017.
Arndt, K. et al., "GCN4 protein, a positive transcription factor in yeast, binds general control promoters at all 5' TGACTC 3' sequences", *Proc. Natl. Acad. Sci. USA*, (1986), 83, 8516-8520.
Baldwin, E. et al., "Thermodynamic and Structural Compensation in "Size-switch" Core Repacking Variants of Bacteriophage T4 Lysozyme", *J. Mol. Biol.* (1996), 259: 542-559.
Chao, H. et al., Kinetic Study on the Formation of a de Novo Designed Heterodimeric Coiled-Coil: Use of Surface Plasmon Resonance to Monitor the Association and Dissociation of Polypeptide Chains:, *Biochemistry* (1996), 35: 12175-12185.
Chenault, H. K. et al., "Kinetic Resolution of Unsaturated and Rarely Occuring Samino Acids: Enanatioselective Hydrolysis of N-Acyl Amino Acids Catalyzed by Acylase I", *J. Am. Chem. Soc.* (1989), I I I, 6354-6364.
Cornish, V. M. et al., "Probing Protein Structure and Function with an Expanded Genetic Code", *Angew. Chem. Int. Ed. Engl.* (1995), 34: 621-633.
d'Avignon, D. A. et al., "Thermodynamic and kinetics of a folded-folded transition at Valine-9 of a GCN4-like leucine zipper", *Biophys. J.* (1999), 76: 2752-2759.
Dahiyat, B.L. et al., "De Novo Protein Design: Fully Automated Sequence Selection" *Science* (1997), 278: 82-87.
DeGrado, W. F. et al., "De Novo Design and Structural Characterization of Proteins and Metalloproteins", *Annu. Rev. Biochem.* (1999), 68: 779-819.
Duewel, H. et al., "Incorporation of Trifluoromethionine into a Phage Lysozyme: Implication and a New Marker for Use in Protein 19F NMR", *Biochemistry* (1997), 36, 3404-3416.
Ellenberger, T. E. et al., "The GCN4 Basic Region Leucine Zipper Binds DNA as a Dimer of Unintterrupted α Helices: Crystal Structure of the Protein-DNA Complex" *Cell* (1992), 71: 1223-1237.
Fersht, A. R. et al., "Principles of protein stability derived from protein engineering experiments", *Curr. Opin. Struct. Biol.* (1993),3: 75-83.
Ghosh, A. et al. "Generalized Born Model Based on a Surface Integral Formulation" *J. Phys. Chem. B*, (1998) 102, 10983-10990.
Giver, L. et al., "Directed evolution of a therostable esterase", *Proc. Natl. Acad. Sci. USA* (1998), 95: 12809-12813.
Gonzales, L. et al., "Crystal structures of a single coiled-coil peptide in two oligomeric states reveal the basis for structural polymorphism", *Nat. Struct. Biol.* (1996), 3: 1002-1100.
Gough, C. A. et al., "Calculations of the relative free energies of aqueous solvation of several fluorocarbons: A test of the bond potential of mean force correction" *J. Chem. Phys.* (1993), 99: 9103-9110.

(Continued)

*Primary Examiner*—Anish Gupta
(74) *Attorney, Agent, or Firm*—Seed IP law Group PLLC

(57) ABSTRACT

The present invention provides a method for producing modified stable polypeptides introducing at least one non-natural amino acid into the hydrophobic region of the polypeptide. The thermal and chemical stability of such polypeptides is improved compared to those properties of its corresponding wild type proteins.

The invention further provides purified leucine zipper and coiled-coil proteins in which the leucine residues have been replaced with 5,5,5-trifluoroleucines, and the modified proteins so produced demonstrate increased thermal and chemical stability compared to their corresponding wild-type natural proteins.

19 Claims, 15 Drawing Sheets

OTHER PUBLICATIONS

Handel, T. M. et al., "Metal Ion-Dependent Modulation of the Dynamics of a Designed Protein", *Science*, (1993), 261: 879-885.

Harbury, P. B. et al., "A Switch Between Two-, Three-, and Four-Stretched Coiled Coils in GCN4 Leucine Zipper Mutants", *Science*, (1993), 262, 1401-1407.

Harpaz, Y. et al., "Volume changes on protein folding", *Structure* (1994), 2: 641-649. (Exhibit 19).

Hill, C. P. et al., "The structure of granulocyte-colony-stimulating factor and its relationship to other growth factors" *Proc. Natl. Acad. Sci. USA* (1993), 90, 5167-5171.

Hine, J. et al., "The Intrinsic Hydrophilic Character of Organic Compounds, Correlations in Terms of Structural Contributions", *J. Org. Chem.* (1975), 40: 292-297.

Hockings, S.C. et al., "Characterization of the ATF/CREB site and its complex with GCN4", *Proc. Natl. Acad. Sci. USA* (1998), 95: 1410-1415.

Keller, P. et al., "Crystal Structure of a Bzip/dna Complex at 2.2 A: Determinants of DNA Specific Recognition", *J. Mol. Biol.* (1995), 254: 657-667.

Kenar, K. T. et al., "A calorimetric characterization of the salt dependence of the stability of the GCN4 leucine zipper", *Protein Sci.* (1995), 4: 1934-1938.

Konig, P. et al., "The X-ray Structure of the GCN4-Bzip Bound to ATF/CREB Site DNA Shows the Complx Depends on DNA Flexibility", *J. Mol. Biol.* (1993), 233: 139-154.

Kono, H. et al., "Designing the hydrophobic core of *Thermus flavus* malate dehydrogenase based on side-chain packing", *Protein Eng.* (1998), 11: 47-52.

Kroll, D. J. et al., "A Multifunctional Prokaryotic Protein Expression System: Overproduction, Affinity Purification, and Selective Detection", *DNA Cell Biol* (1993), 12: 441-53.

Krylov, D. et al., "A thermodynamic scale for leucine zipper stability and dimerization specificity: e and g interhelical interactions", *EMBO J.* (19940, 13: 2849-2861.

Lee, B. et al., "Stability of protein structures", *Curr. Opin. Biotech.* (1997), 8: 423-426.

Lim, K-T. et al., "Molecular Dynamics for Very Large Systems on Massively Parallel Computers: The MPSim program", *J. Comp. Chem.* (1997), 18: 501-521.

Lubienski, M. J. et al., "Three-Dimensional Solution Structure and $^{13}$C Assignments of Barstar Using Nuclear Magnetic Resonance Spectroscopy", *Biochemistry* (1994), 33: 8866-8877.

Lumb, K. J. et al., "Measurement of Interhelical Electrostatic Interactiona in the GCN4 Leucine Zipper", *Science* (1995), 268: 436-438.

Matthews, B. W. "Studies on Protein Stability with T4 Lysozyme", *Adv. Protein Chem.* (1995), 46: 249 1995.

Mendel, D. et al., "Probing Protein Stability with Unnatural Amino Acids", *Science* (1992), 256, 1798-1802.

Mer, G. et al., "Stablization of proteins by glycosylation examined by NMR analysis of a fucosylated proteinase inhibitor", *Nat. Struct. Biol.* (1996), 3: 45-53.

Metallo, S. J. et al., "Distribution of labor among bZIP segments in the control of DNA affinity and specificity", *Chem. Biol.* (1994), 1: 143-151.

Mohanty, D. et al., "DeNovo Simulations of the Folding Thermodynamics of the GCN4 Leucine Zipper", *Biophys. J.* (1999), 77: 54-69.

Moitra, J. et al., "Leucine is the Most Stabilizing Aliphatic Amino Acid in the d Position of a Dimeric Leucine Zipper Coiled Coil", *Biochemistry* (1997), 36: 12567-12573.

Nautiyal, S. et al., "Crystal structure of a designed, thermostable, heterotrimeric coiled coil", *Protein Sci.* (1999), 8: 84-90.

O'Shea, E. K. et al., "X-ray Structure of the GCN-4 Leucine Zipper, a Two-Stranded, Parallel Coiled Coil", *Science* (1989), 254: 538-542.

O'Shea, E. K. et al., "Evidence that the Leucine Zipper is a Coiled Coil", *Science* (1991), 254: 539-544.

Paolella, D. N. et al., "DNA Targets for Certain Bzip Proteins Distinguished by an Intrinsic Bend", *Science* (1994), 264: 1130-1133.

Petka, W. A. et al., "Reversible Hydrogels from Self-Assembling Artificial Proteins", *Science* (1998), 281: 389-392.

Rennert, O. M. et al., "On the Incorporation of 5', 5', 5'-Trifluoroleucine into Proteins of *E. coli*", *Biochemistry* (1963), 2: 471-476.

Roux, M. et al., "Fragmentation of Phospholipid Bilayers by Myelin Basic Protein", *Biochemistry* 33: 307 1994.

Sandberg, W. et al., "Influence of Interior Packing and Hydrophobicity on the Stability of a Protein", *Science* (1989), 245: 54-57.

Schneider, J. P. et al., "A Designed Buried Salt Bridge in a Heterodimeric Coiled Coil", *J. Am. Chem. Soc.* (1997), 119: 5742-5743.

Sharma, N. et al., "Efficient introduction of aryl bromide functionality into proteins in vivo", *FEBS Lett.* (2000), 467: 37-40.

Southern, E. M. "Detection of Specific Sequences among DNA Fragments Separated by Gel Electrophoresis", *J Mol Biol.* (1975), 98:503-517.

Tannor, D. J. et al., "Accurate First Principles Calculation of Molecular Charge Distributions and Solvation Energies from Ab initio Quantum Mechanics and Continuum Dielectric Theory", *J. Am. Chem. Soc.*, (1994), 116: 11875-11882.

Thompson, K. S. et al., "Thermodynamic Characterization of the Structural Stability of the Coiled-Coil Region of the Bzip Transcription Factor GCN4", *Biochemistry* (1993), 32: 5491-5496.

van Hest, J. C. M. et al., "Efficient introduction of alkene functionality into proteins in vivo", *FEBS Lett.*, (1998), 428: 68-70.

van Hest, J. C. M. et al., "Efficient Incorporation of Unsaturated Methionine Analogs into Proteins in Vivo", *J. Am. Chem. Soc.* (2000), 122: 1282-1288.

Wendt, H. et al., "Kinetics of Folding of Leucine Zipper Domains", *Biochemistry* (1995), 34: 4091-4107.

Wigler, M. et al., "DNA-mediated transfer of the adenine phosphoribosyltransferase locus into mammalian cells", *Proc Natl Acad Sci USA* (1979), 76:1373-76.

Zhang, X-J. et al., "Enhancement of Protein Stability by the combination of point mutations in T4 lysozyme is additive", *Protein Eng.* (1995), 8: 1017-1022.

Zhang, C. et al., "Asymmetric Synthesis of (S)-5,5,5,5',5',5'-Hexafluoroleucine", *Helv. Chim. Acta* (1998), 81: 174-181.

Zhou, Y. et al., "Building a Thermostable Membrane Protein", *J. Biol. Chem.* (2000), 275: 6975-6979.

\* cited by examiner

R MKQLEDK VEELLSK NYHLENE VARLKKL VGER

Figure 1A

Leucine　　　　　　Trifluoroleucine　　　　　　Hexafluoroleucine

MRGSHHHHHHGSMA SGDLENE YAQLERE VRSLEDE AAELEQK
VSRLKNE IEDLAEI GDLNNTSGIRRPAAKLN

Figure 4A

METHOD FOR STABILIZATION OF PROTEINS USING NON-NATURAL AMINO ACIDS

Under 35 USC § 120, this application is a continuation application of U.S. application Ser. No. 09/620,691, filed Jul. 20, 2000, now pending, which claims the benefit under 35 USC § 119(e) of U.S. Provisional Application No. 60/191, 640, filed Mar. 23, 2000, now abandoned. The disclosure of each of the prior applications is considered part of and is incorporated by reference in the disclosure of this application.

Throughout this application various publications are referenced. The disclosures of these publications in their entireties are hereby incorporated by reference into this application in order to more fully describe the state of the art to which this invention pertains.

FIELD OF THE INVENTION

The present invention relates to improved stabilization of polypeptides by incorporation of non-natural amino acids, such as hyper-hydrophobic amino acids, into the hydrophobic core regions of the polypeptides.

BACKGROUND OF THE INVENTION

Engineering of stable enzymes and robust therapeutic proteins is of central importance to the biotechnology and pharmaceutical industries. The primary internal driving forces for stabilizing proteins involve various interactions such as desolvation, electrostatic interaction, hydrogen bonding, and van der Waal forces, and a proper balance of these interactions is necessary for the appropriate folding of a protein. Although protein engineering provides powerful tools for the enhancement of enzymatic activity and protein stability (J. L. Cleland, C. S. Craik, *Protein Engineering: Principles and Practice* (Wiley-Liss, New York, N.Y., 1996); D. Mendel, J. A. Ellman, Z. Y. Chang, D. L. Veenstra, P. A. Kollman, *Science* 256, 1798 1992; A. R. Fersht, L. Serrano, *Curr. Opin. Struct. Biol.* 3, 75 1993; B. W. Matthews, *Adv. Protein Chem.* 46, 249 1995), the scope of engineering of proteins is limited by the functionality offered by the twenty naturally occurring proteinogenic amino acids (V. W. Cornish, D. Mendel, P. G. Schultz, *Angew. Chem. Int. Ed. Engl.* 34, 621, 1995), permitting only modest and unpredictable gains in stability by modifying the protein sequence.

Non-natural amino acids that contain unique side chain functional groups including halogens, unsaturated hydrocarbons, heterocycles, silicon, organometallic units, can offer advantages in improving the stability of the folded structure of proteins without requiring sequence modifications. Functionalities orthogonal to that of the naturally occurring amino acids, including alkenes (van Hest, J. C. M. et al., 1998. *FEBS Lett.,* 428, 68-70), alkynes (van Hest, J. C. M.; Kiick, L. K.; Tirrell, D. A. *J. Am. Chem. Soc.* 2000, 122, 1282-1288), aryl halides (Sharma, N.; Furter, R.; Kast, P.; Tirrell, D. A. *FEBS Lett.* 2000, 467, 37-40) and electroactive side chains (Kothakota, S.; Fournier, M. J.; Tirrell, D. A.; Mason, T. L. *J. Am. Chem. Soc.* 1995, 117, 536-537) have been incorporated into proteins prepared in bacterial cultures. Trifluoromethionine has been inserted into bacteriophage lambda lysozyme in vivo and serves as a unique probe for $^{19}$F NMR spectroscopy (Duewel, H.; Daub, E.; Robinson, V.; Honek, J. F. *Biochemistry* 1997, 36, 3404-3416). Trifluoroleucine was reported more than 30 years ago to support bacterial cell growth and to be incorporated into nascent proteins in the absence of leucine during biosynthesis (Rennert, O. M.; Anker, H. S. *Biochemistry* 1963, 2, 471). In addition, substitution of amino acids such as serine or alanine that normally comprise the hydrophillic region(s) of the proteins, but are also present, to a lesser degree, in the hydrophobic regions, with the fluoro derivatives is likely to result in stronger inter-helical interaction, thus resulting in improved stability.

Leucine-zipper domains occur commonly in protein assemblies such as eukaryotic transcription factors (O'Shea, E. K, Rutkowski, R., Kim, P. S. *Science* 1989, 243, 538-542; Lumb, K. J, Kim, P. S. *Science* 1995, 268, 436-438; Wendt, H., Baici, A., Bosshard, H. R.; *J. Am. Chem. Soc.* 1994, 116, 6073-6074; Gonzales, L., Brown, R. A., Richardson, D., Alber, T. *Nat. Struct. Biol.* 1996, 3, 1002-1100; Kenar, K. T., Garcia-Moreno, B., Freire, E. *Protein Sci.* 1995, 4, 1934-1938; Mohanty, D., Kolinski, A., Skolnick, J. *Biophys. J.* 1999, 77, 54-69; d'Avignon, D. A., Bretthorst, G. L., Holtzer, M. E., Holtzer, A. *Biophys. J.* 1999, 76, 2752-2759). Such domains form coiled-coil structures comprising generic heptad repeats designated abcdefg, where the d positions are occupied predominantly by leucine residues. The thermodynamics (Thompson, K. S., Vinson, C. R., Freire, E. *Biochemistry* 1993, 32, 5491-5496; Krylov, D, Mikhailenko, I., Vinson, C. *EMBO J.* 1994, 13, 2849-2861), kinetics (Wendt, H., Berger, C., Baici, A., Thomas, R. M., Bosshard, H. R. *Biochemistry* 1995, 34, 4091-4107; Chao, H., Houston, M. E., Grothe, S., Kay, C. M., O'Connor-McCourt, M., Irvin, R. T., Hodges, R. S. *Biochemistry* 1996, 35, 12175-12185) and structural features (O'Shea, E. K., Klemm, J. D., Kim, P. S., Alber, T. *Science* 1991, 254, 539-544; Nautiyal, S., Alber, T., *Protein Sci.* 1999, 8, 84-90; Harbury, P. B., Zhang, T., Kim, P. S., Alber, T. *Science,* 1993, 262, 1401-1407) of leucine zipper peptides have been characterized extensively. Studies in which leucine residues at the d positions have been replaced by other naturally occurring aliphatic amino acids have demonstrated that leucine is the most effective amino acid in terms of stabilization of the coiled-coil structure (Moitra, J., Szilak, L., Krylov, D., Vinson, C. *Biochemistry* 1997, 36, 12567-12573; Hodges, R. S., Zhou, N. E., Kay, C. M., Semchul, P. D. *Peptide Research,* 1990, 3, 125-137). In fact, leucine is the most abundant amino acid in cellular proteins spanning a wide range of organisms (Creighton, T. E. *Proteins Structures and Molecular Properties*; W. H. Freeman and Company: New York, 1993). Leucine-enriched hydrophobic cores are important in driving protein folding and determining protein stability in a large number of proteins (Lubienski, M. J., Bycroft, M., Freund, S. M. V., Fersht, A. R. *Biochemistry* 1994, 33, 8866-8877; Hill, C. P., Osslund, T. D., Eisenberg, D. *Proc. Natl. Acad. Sci. USA* 1993, 90, 5167-5171).

Previous examples of employing other natural amino acids as an attempt to replace leucine have all resulted in loss in coiled coil stability (Moitra, J.; Szilak, L.; Krylov, D.; Vinson, C. *Biochemistry* 1997, 36, 12567-12573; Hodges, R. S.; Zhou, N. E.; Kay, C. M.; Semchul, P. D.; *Peptide Research,* 1990, 3, 125-137). This is largely due to the fact that these substitutions are usually the "large" to "small" type and can result in loss of protein hydrophobic core packing efficiency (Sandberg, W.; Terwilliger, T. *Science* 1989, 245, 54-57; Baldwin, E.; Xu, J.; Hajiseyedjavadi, O.; Baase, W. A.; Matthews, B. W. *J. Mol. Biol.* 1996, 259, 542-559; Kono, H.; Nishiyama, M.; Tanokura, M.; Doi, J. *Protein Eng.* 1998, 11, 47-52). Protein cores are believed to be tightly packed and require a jigsaw puzzle-like arrangement of different residue side chains (Harpaz, Y., Gerstein, M.; Chothia, C. *Structure* 1994, 2, 641-649; Richards, F. M., Lim, W. A. *Q. Rev. Biophys.* 1994, 15, 507-523; Levitt, M., Gerstein, M., Huang, E., Subbiah, S., Tsai, J. *Annu. Rev. Biochem.* 1997, 66, 549-579).

Thus any perturbation with amino acids of slight difference in geometry can result in substantial energetic cost.

The present invention provides a unique strategy to systematically target the hydrophobic core region(s) of proteins, wherein naturally occurring hydrophobic amino acids are replaced with hyper-hydrophobic non-natural amino acids, resulting in the creation of novel artificial polypeptides, which are identical to the corresponding natural proteins in their tertiary structure and function, but offer an additional advantage of increased stability relative to the corresponding wild type proteins.

SUMMARY OF THE INVENTION

The present invention provides methods to improve the stability of proteins by incorporating one or more non-natural amino acids into the hydrophobic core region(s) of existing protein structures. The thermal and chemical stability of such proteins having the non-natural amino acids is significantly improved compared to those of corresponding wild-type proteins.

The invention further provides purified leucine zipper and coiled-coil polypeptides in which the leucine residues have been replaced with 5,5,5-trifluoroleucines, and the modified proteins so produced. These proteins demonstrate increased thermal and chemical stability compared to their corresponding wild type natural proteins.

BRIEF DESCRIPTION OF THE FIGURES

FIG. 1a shows: Amino acid sequence of GCN4-p1.

FIG. 4a shows Amino acid sequence of a leucine-zipper peptide designated A1. The leucine positions are highlighted in bold.

Figure 1B:
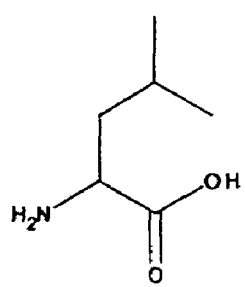
FIG. 1b shows the structures of leucine, trifluoroleucine (Tfl) and hexafluoroleucine (Hfl).
Figure 1B:
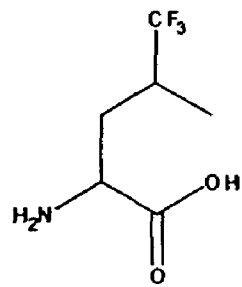
Figure 1B:
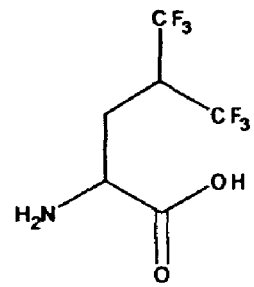
Figure 1C:
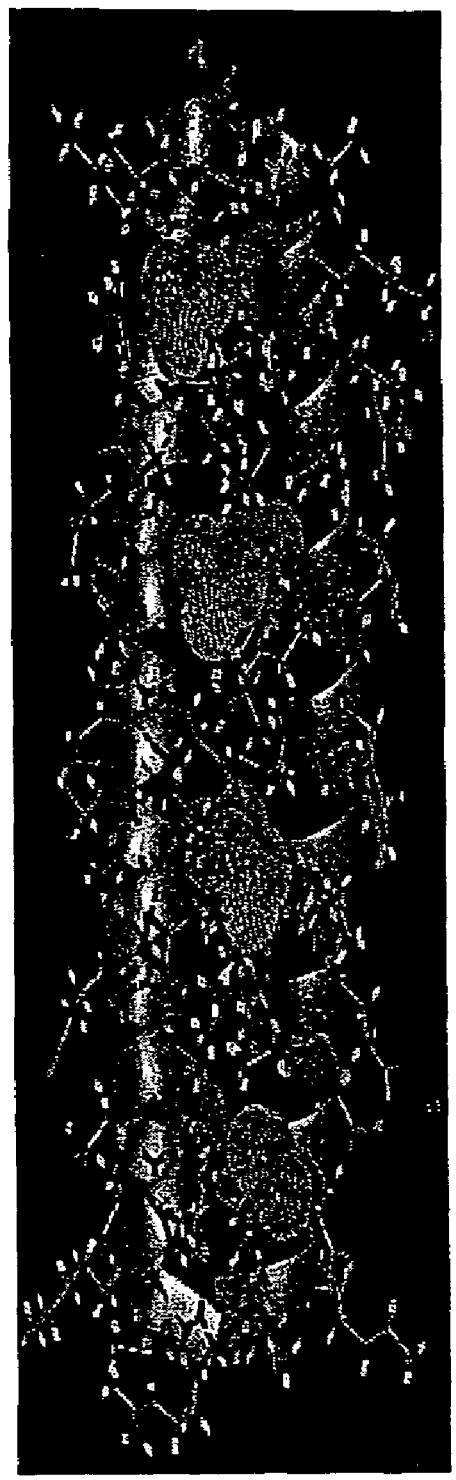
FIG. 1c shows three-dimensional representation of the dimeric GCN4-p1 substituted with trifluoroleucine at the four d-positions in the helix.

The fraction of unfolded protein is plotted against increasing urea concentration. Insert: The urea concentration at which 50% of protein is denatured is plotted against the extent of fluorination. (10 μM protein concentration, PBS buffer, pH 7.4).

DETAILED DESCRIPTION OF THE INVENTION

Definitions

As used in this application, the following words or phrases have the meanings specified.

As used herein, "natural" or "wild type" refers to a protein or a polypeptide, which is found in nature, and "artificial" refers to a protein or a polypeptide that comprises non-natural sequences and/or amino acids.

As used herein, the term "non-natural amino acid" refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality.

As used herein, the term "hyper-hydrophobic" means that the non-natural amino acid is more hydrophobic than the corresponding natural amino acid. The examples of hyper-hydrophobic amino acids include trifluoroleucine, hexafluoroleucine, didehydroleucine, trifluorovaline, hexafluorovaline.

As used herein, the term "$T_m$" means the temperature at which 50% of the peptide has unfolded.

As used herein, the term "$C_m$" means the detergent concentration at which 50% of the peptide has unfolded.

Method of the Invention

The present invention provides methods to improve the stability of proteins by incorporating one or more non-natural amino acids into the hydrophobic core region(s) of existing protein structures. Improved stability refers to the presence of a higher ratio of folded to unfolded protein relative to that of the wild type protein. Improved stability can be determined by examining the amount of folded protein present under varying conditions of temperature, detergent, and pH.

Protein folding is driven by a variety of interactions including desolvation, H-bonding, electrostatic interaction and van der Waal forces, and there is a general tendency of protein structures to bury the hydrophobic amino acids away from water. By changing the naturally occurring hydrophobic amino acids to hyper-hydrophobic amino acid analogs, it is believed that the proteins' tendency to remain folded will increase. This strategy can be applied to almost any protein because all protein folding are driven by this tendency. Proteins that could be evaluated for increased stability using this approach include proteins containing leucine-zipper domains, membrane proteins, cytokines and enzymes (M. Roux, F. Nezil, M. Monck, M. Bloom, *Biochemistry* 33, 307 1994). Proteins such as small membrane peptides that rely on hydrophobic side chains to form ion channels in membranes may particularly benefit from increased membrane or interpeptide association offered by the methods of this invention. Furthermore, this approach will be especially useful for designing enzymes that can function in non-aqueous medium, such as in organic solvents (Gladilin, A. K., Levashov, A. V., Biochemistry (Mosc), 1998, 63, 345-356: Gupta, M. N., Europ. J. Biochem, 1992, 203, 25-32).

The non-natural amino acids incorporated into polypeptides using the method of this invention are different from the twenty naturally occurring amino acids in their side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods such as, but not limited to, in vivo incorporation of the non-natural amino acid by expression of the cloned gene in a suitable host.

In a preferred embodiment, the non-natural amino acids used are the fluorinated amino acids including trifluoroleucine and hexafluoroleucine. In one embodiment, by replacing leucine with e.g., trifluoroleucine in a polypeptide of the leucine zipper family, leucine zipper peptides and proteins gain stability with respect to thermal and chemical denaturation. The choice of fluorinated amino acids is based on several factors, the most important of which is the observation that many fluorocarbons behave as though they are more hydrophobic than their hydrocarbon analogs (Gough, C. A.; Pearlman, D. A.; Kollman, P. *J. Chem. Phys.* 1993, 99, 9103-9110; Hine, J., Mookejee, P. K. *J. Org. Chem.* 1975, 40, 292-297). Second, because the trifluoromethyl group is chemically inert and nearly isosteric to the methyl group, its insertion into the helical interface does not disrupt the arrangement of the hydrophobic pocket around what was previously a methyl group (Kukhar, V. P., Soloshonok, V. A. *Fluorine Containing Amino Acids—Synthesis and Properties*; John Wiley & Sons: Chichester, 1995), suggesting that proteins and peptides outfitted with fluorinated amino acids might adopt folded structures similar to those of their corresponding "wild type" proteins.

In a specific example, using two α-helical polypeptides, GCN4-p1, and A1 as model peptides, protein stability was significantly increased by incorporating the hyper-hydrophobic non-natural amino acids. The proteins used in this example, are of the leucine-zipper family, in which stability and folding are highly dependent on the core leucine residues. From the X-ray crystal structure analysis of the GCN4-p1 leucine zipper peptide, it is known that the branched side chains on opposing leucine residues in a leucine zipper are in a side by side configuration (O. M. Rennert, H. S. Anker, *Biochemistry* 2, 471, 1963; S. Kothakota, M. J. Dougherty, M. J. Fournier, T. L. Mason, D. A. Tirrell, *Macromol. Symp.* 98, 573, 1995). The methyl groups of leucines provide stabilizing effects by efficiently packing with the many adjacent hydrophobic regions between the α-helices. Because trifluoromethyl groups are isosteric to methyl groups, their insertions into the helical interface do not disrupt the arrangement of the hydrophobic pocket around what was previously a methyl group.

Proteins and Polypeptides of the Invention

The protein and polypeptides to be stabilized may be isolated from any source whether natural, synthetic, semi-synthetic, or recombinant. As defined elsewhere in this application "natural" or "wild type" refers to a protein or a polypeptide, which is found in nature, and "artificial" refers to a protein or a polypeptide that comprises non-natural sequences and/or amino acids.

The suitable non-natural amino acids for use in this invention include, but are not limited to, molecules having fluorinated, electroactive, and unsaturated side chain functionalities. Non-natural amino acid analogs and derivatives for leucine include but are not limited to 5,5,5-trifluoroleucine, 5,5,5,5',5',5'-hexafluoroleucine, and 2-amino-4-methyl-4-pentenoic acid. Non-natural amino acid analogs and derivatives for isoleucine include but are not limited to 2-amino-3, 3,3-trifluoro-methylpentanoic acid, 2-amino-3-methyl-5,5, 5-trifluoropentanoic acid, and 2-amino-3-methyl-4-pentenoic acid. Non-natural amino acid analogs and derivatives for valine include but are not limited to trifluorovaline and hexafluorovaline. Non-natural amino acid analogs for methionine include but are not limited to 6,6,6-trifluoromethionine, homoallyglycine, and homoproparglyglycine. However, a similar strategy for incorporating the halogen containing non-natural amino acid analog for phenylanine such as p-fluoro- phenylalanine and p-bromophenylalanine may be less useful for protein stabilization since presence of electron withdrawing groups such as fluorine may alter the conjugated phenyl ring of phenyl alanine.

The proteins and polypeptides that can be targeted for stabilization using the method of the invention are those possessing a hydrophobic core region. These include, but are not limited to, cytokines such as interleukins, Tumor Necrosis Factor, Granulocyte Colony Stimulating Factor, Erythropoitin, proteases such as Subtilisin, Thermolysin, industrial enzymes such as dehydrogenases, estrases. Since most of these proteins are comprised of helix bundles, their structure can be stabilized by incorporating non-natural hyper-hydrophobic amino acids into the hydrophobic core region(s) of the target protein.

The protein site(s) targeted for incorporating non-natural amino acids include region(s) containing hydrophobic amino acids that generally drive protein folding. The specific hydrophobic amino acids that are target of this invention include leucine, isoleucine, valine, and to a lesser degree methionine and phenylalanine.

The proteins of the present invention can be made either by chemical synthesis or by utilizing recombinant DNA technology as described in the Examples 2 and 3. The principles of solid phase chemical synthesis of polypeptides are well known in the art and may be found in general texts relating to this area (Dugas, H. and Penney, C. 1981 *Bioorganic Chemistry*, pp 54-92, Springer-Verlag, New York). Wild type and artificial proteins and polypeptides can be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Recombinant Nucleic Acid Molecules Comprising Nucleotide Sequences Encoding a Polypeptide of Interest Also provided are recombinant nucleic acid molecules, such as recombinant DNA molecules (rDNAs) that contain nucleotide sequences encoding a polypeptide of the invention such as a leucine zipper protein, or a coiled-coil protein, or fragments thereof that incorporate at least one non-naturally occurring amino acid. As used herein, a rDNA molecule is a DNA molecule that has been subjected to molecular manipulation in vitro. Methods for generating rDNA molecules are well known in the art, for example, see Sambrook et al., *Molecular Cloning* (1989), supra.

Vectors

The term vector includes, but is not limited to, plasmids, cosmids, and phagemids. A preferred vector for expression will be an autonomously replicating vector comprising a replicon that directs the replication of the rDNA within the appropriate host cell. The preferred vectors also include an expression control element, such as a promoter sequence, which enables transcription of the inserted sequences and can be used for regulating the expression (e.g., transcription and/or translation) of an operably linked sequence in an appropriate host cell such as *Escherichia coli*. Expression control elements are known in the art and include, but are not limited to, inducible promoters, constitutive promoters, secretion signals, enhancers, transcription terminators, and other transcriptional regulatory elements. Other expression control elements that are involved in translation are known in the art, and include the Shine-Dalgarno sequence, and initiation and termination codons. The preferred vector also includes at least one selectable marker gene that encodes a gene product that confers drug resistance, such as resistance to ampicillin or tetracyline. The vector also comprises multiple endonuclease restriction sites that enable convenient insertion of exogenous DNA sequences.

The preferred vectors for generating the encoded "wild type" or "artificial" polypeptides are expression vectors, which are compatible with prokaryotic host cells. Prokaryotic cell expression vectors are well known in the art and are available from several commercial sources. For example, a pQE vector (e.g., pQE15, available from Qiagen Corp.) may be used to express "wild type" polypeptides, containing natural amino acids and "artificial" polypeptides, including those containing non-natural amino acids, in bacterial host cells.

Fusion genes

A fusion gene includes a sequence encoding a polypeptide of the invention operatively fused (e.g., linked) to a nonrelated sequence such as, for example, a tag sequence to facilitate isolation and/or purification of the expressed gene product (Kroll, D. J., et al., 1993 *DNA Cell Biol.* 12:441-53). The pQE expression vectors used in this invention express proteins fused to a poly-Histidine tag that facilitates isolation and/or purification of the expressed gene.

Transformed Host Cells

The invention further discloses a host-vector system comprising the vector, plasmid, phagemid, or cosmid having a nucleotide sequence encoding the polypeptide of invention, introduced into a suitable host cell. The host-vector system can be used to produce the polypeptides encoded by the inserted nucleotide sequences. The host cell can be either prokaryotic or eukaryotic. Examples of suitable prokaryotic host cells include bacterial strains from genera such as *Escherichia, Bacillus, Pseudomonas, Streptococcus,* and *Streptomyces*. Examples of suitable eukaryotic host cells include a yeast cell, a plant cell, or an animal cell, such as a mammalian cell. A preferred embodiment provides a host-vector system comprising the pQE15 vector having a sequence encoding the polypeptide of invention, which is introduced along with the pREP4 vector into an appropriate auxotroph such as *E. coli* leucine auxotroph SG13009 strain, which is useful, for example, for producing a polypeptide where leucine residues are replaced with a non-natural amino acid.

Introduction of the rDNA molecules of the present invention into an appropriate cell host is accomplished by well known methods that typically depend on the type of vector used and host system employed. For transformation of prokaryotic host cells, electroporation and salt treatment methods are typically employed, see for example, Cohen et al., 1972 *Proc Acad Sci USA* 69:2110; Maniatis, T., et al., 1989 *Molecular Cloning, A Laboratory Manual*, Cold Spring Harbor Laboratory, Cold Spring Harbor, N.Y. Transformation of vertebrate cells with vectors containing rDNAs, electroporation, cationic lipid or salt treatment methods, is typically employed, see, for example, Graham et al., 1973 *Virol* 52:456; Wigler et al., 1979 *Proc Natl Acad Sci USA* 76:1373-76.

Successfully transformed cells, i.e., cells that contain a rDNA molecule of the present invention, are identified by well-known techniques. For example, cells resulting from the introduction of a rDNA of the present invention are selected and cloned to produce single colonies. Cells from those colonies are harvested, lysed and their DNA content examined for the presence of the rDNA using a method such as that described by Southern, *J Mol Biol* (1975) 98:503, or Berent et al., *Biotech* (1985) 3:208, or the proteins produced from the cell are assayed via a biochemical assay or immunological method such as Western blotting.

Recombinant methods are preferred if longer proteins, higher yield, or a controlled degree of non-natural amino acid incorporation is desired. Recombinant methods involve expressing the cloned gene in a suitable host cell. For example, a suitable host cell is introduced with an expression vector having the nucleotide sequence encoding the protein of interest. The host cell is then cultured under conditions that permit in vivo production of the desired protein, wherein one or more naturally occurring amino acids in the desired protein or polypeptide are replaced with the non-natural amino acid analogs and derivatives. In many applications, for example, when replacing leucine with a fluorinated amino acid analog, it may be desirable to achieve only partial incorporation of the fluorinated amino acid in the hydrophobic core because fully fluorinated proteins are usually obtained in lower yields and may compromise in activity. Therefore it is important to be able to control the levels of incorporation of non-natural amino acid so that the protein stability, activity and yields are all optimal.

Advantages of the Invention

This invention introduces a unique strategy that can be widely applied to stabilize the folded structure of proteins and polypeptides under normally denaturing conditions. Proteins and polypeptides modified using the method of this invention exhibit higher stability under denaturing conditions such as elevated temperature, presence of denaturing chemicals, extreme solution pH and other non-physiological environments.

The method of this invention changes the building blocks of protein synthesis, leaving the "blueprint" encoding the proteins unchanged. This invention, therefore, permits a rapid and predictable approach to design and produce proteins and polypeptides with significantly increased stability.

This method of this invention is generally applicable to a large range of proteins, enzymes, and peptides, and is not limited by size or structure. For example, the incorporation of hyper-hydrophobic amino acids such as the fluorinated amino acids results in very minimal perturbation of the protein structure, and the inert nature of the fluorinated side-chains will leave many protein functions unchanged. The catalytic, signaling, or inhibitory activities of proteins containing non-natural amino acids, should not be compromised at the expense of increased stability.

Incorporation of hyper-hydrophobic amino acids should be especially useful for stabilizing small membrane peptides that rely on hydrophobic side chains to form ion channels in membranes and may also benefit from increased membrane (or inter-peptide) association upon fluorination. Furthermore, the feasibility of incorporating fluorinated amino acids using the in vivo methods should allow the fluorination of enzymes, signaling molecules, protein ligands, and may prove to be of broad utility in the engineering of more robust biological assemblies.

The following examples are presented to illustrate the present invention and to assist one of ordinary skill in making and using the same. The examples are not intended in any way to otherwise limit the scope of the invention.

EXAMPLE 1

The following Example provides a description of how the non-natural amino acid analogs trifluoroleucine (Tfl) and hexafluoroleucine (Hfl) were prepared.

Trifluoroleucine (Tfl, FIG. 1B) was synthesized in an overall yield of 22% in seven steps starting from β-trifluoromethylcrotonic acid (Oakwood Chemical, Columbia, S.C.), according to the procedure of Rennert et al. with slight modifications (Rennert, O. M.; Anker, H. S. *Biochemistry* 1963, 2, 471). DL-trifluoroleucine prepared by this method as the N-acetylated racemic mixture was resolved to L-trifluoroleucine by treatment with porcine kidney acylase (Sigma) to >99% enantiomeric excess (e.e). (Chenault et al. *J. Am. Chem. Soc.* 111, 6354-6364, 1989). The yield for the resolution was 67%. The determination of e.e. was accomplished by $^1$H NMR spectroscopy following derivatization with Mosher's acid, R-(+)-methoxytrifluoromethylphenylacetic acid.

Hexafluoroleucine (Hfl, FIG. 1B) was prepared by modification of the procedures reported by Zhang et al. (Zhang, C.; Ludin, C.; Eberle, M. K.; Stoeckli-Evans, H.; Keese, R. *Helv. Chim. Acta* 1998, 81, 174-181).

EXAMPLE 2

The following Example provides a description of the chemical synthesis of "wild type" (Leu-GCN4-p1) and trifluoleucine incorporated (Tfl-GCN4-p1) forms of the leucine zipper peptide Leu-GCN4-p1.

The amino acid sequence of GCN4-p1 is shown in FIG. 1A. Both the "wild type" (Leu-GCN4-p1) and fluorinated (Tfl-GCN4-p1) forms of the leucine zipper peptide GCN4-p1 were synthesized at the Biopolymer Synthesis Center at the California Institute of Technology (Pasadena, Calif. 91125). Automated, stepwise solid-phase synthesis was performed on an ABI 433A synthesizer employing Fmoc chemistry. To prepare the fluorinated peptide (Tfl-GCN4-p1), N-Fmoc-5,5,5-trifluoro-L-leucine prepared as described in Example 1 was used as an equimolar mixture of the 2S,4S- and the 2S,4R-isomers, and incorporated into the peptide with extended coupling cycles. After chain assembly was complete, the peptide was deprotected and removed from the resin support with trifluoroacetic acid in the presence of 1,2-ethanedithiol, thioanisole and water. Peptides were precipitated into cold methyl t-butyl ether and isolated by centrifugation. Peptide products were purified by preparative $C_{18}$ reverse phase HPLC using a non-linear gradient of 0-80% elution solution (0.1% TFA/60% acetonitrile/40% $H_2O$) in 120 min. Neither Leu-GCN4-p1 nor Tfl-GCN4-p1 is acylated at the N-terminus; hence the thermal melting temperature of Leu-GCN4-p1 is lower than that reported for acylated GCN4-p1. After HPLC purification, the molar mass of Tfl-GCN4-p1 was confirmed to be 4213 Da, 216 mass units higher than that of Leu-GCN4-p1.

EXAMPLE 3

The following Example provides a description of the procedure used to express in *E. coli* cells, the "wild type" proteins and the corresponding "artificial" proteins of the invention, in which the leucine residues are replaced with a non-natural fluorinated amino acid.

Analog Incorporation Assay. The expression vector pQE-A1, which contains the coding sequences for the protein A1 (FIG. 4A) was obtained from US Army Natick RD&E Center (Natick, Mass.). The *E. coli* leucine auxotroph SG13009 was obtained from Qiagen (Chatsworth, Calif.) and transformed with plasmids pREP4 and pQE-A1, to yield the expression host LAE-A1.

Figure 4B:
FIG. 4b shows western blot analysis of A1 expression by E. coli. Lane 1: uninduced sample; lane 2: induced sample without supplementation; lane 3: induced sample supplemented with leucine; lane 4: induced sample supplemented with 2; lane 5: induced sample supplemented with 3, as described in Example 7.

M9AA medium (30 ml) supplemented with 1 mM $MgSO_4$, 1 mM $CaCl_2$, 20 wt % glucose, 1 mg/L thiamin and the antibiotics ampicillin (200 mg/L) and kanamycin (25 mg/L) were inoculated with 1 ml of an overnight 2×YT culture of the expression strain. After the culture had grown to an $OD_{600}$ of 1.0 at 37° C., the cells were collected by centrifugation at 5,000 g for 10 min at 4° C. The supernatant was removed and the cell pellets were washed with 0.9% NaCl and sedimented (5000 g, 10 min, 4° C.). The washing and sedimentation steps were repeated three times to remove residual leucine. The washed cells were then resuspended in 31 ml of supplemented M9AA medium, without leucine. Aliquots (5 ml) were added to test tubes containing no leucine (negative control), L-leucine (20 mg/L, positive control), DL-trifluoroleucine (40 mg/L) or DL-hexafluoroleucine (40 mg/L). The cultures were grown for 10 min at 37° C., and isopropyl-β-D-thiogalactopyranoside (IPTG) was added to a final concentration of 1 mM. The cultures were grown for 3 hours and cells were collected by sedimentation (13,000 g, 1 min, 4° C.). Cell pellets were resuspended in Buffer A (8 M urea, 0.1 M $NaH_2PO_4$, 0.01 M Tris, pH 8.0) and were frozen immediately. The whole cell lysate was analyzed by 15% SDS-PAGE. The proteins were detected by western blotting with an antibody specific for the N-terminal His-Tag of A1 (FIG. 4B).

Protein Expression and Purification. M9 medium (1 L) supplemented as described above was inoculated with 30 ml of fresh overnight culture of the expression strain. After the culture had grown to $OD_{600}$ of 1.0, it was subjected to centrifugation and washing procedures as described above. The cell pellet was suspended in 1 L M9 medium supplemented with trifluoroleucine (100 mg/L) and leucine in appropriate concentrations. IPTG was added after 10 min to induce protein expression. The expression of protein was monitored by removing an aliquot (1 ml) of the culture every hour and analyzing by SDS-PAGE. Cells were collected after 3 hr by centrifugation (5000 g, 15 min, 4° C.). The pellets were resuspended in 20 ml of buffer A and stored at −80° C. overnight. The cells were thawed rapidly at 37° C., cell debris was sedimented (22,500 g, 50 min, 4° C.), and the supernatant was applied to Ni-NTA column (1 cm×5 cm) (*The Qiagen Expressionist, Purification Procedure*, 1992, pp 45). The column was washed with 25 ml each of buffer A at pH 8.0, 6.5 and 5.9, sequentially. The target protein was eluted at pH 4.5. Fractions containing protein were combined and dialyzed (Spectra/Por membrane, MWCO at 3.5 kDa) against sterile water for 3 days. The dialysate was lyophilized to yield pure A1. The purity of the protein was examined by SDS-PAGE (15%) (FIG. 4B). Extent of trifluoroleucine incorporation was determined by amino acid analysis (DNA/Protein Analysis Facility, Cornell University) and MALDI mass spectrometry (Protein/Peptide Micro Analytical Laboratory, Caltech).

EXAMPLE 4

The following Example describes procedures used for the biochemical characterization of wild-type proteins and the corresponding artificial proteins of the invention in which the leucine residues were replaced with non-natural amino acids.

Ultracentrifugation. Sedimentation equilibrium analysis of the wild type proteins GCN4-p1 and A1 and the corresponding artificial proteins containing the non-natural amino acids was performed using a Beckman XLI analytical ultracentrifuge, recording interference data and radial absorbance at 236 and 280 nm at the same time. Initial peptide concentrations ranged between 100 and 300 µM; buffer was 0.01 M sodium phosphate, pH 7.4, containing 0.1 M NaCl. The samples were centrifuged at 35000, 40000, 45000 rpm, until equilibrium was reached. Partial specific volumes were calculated by the residue-weighted average method of Cohn and Edsall (Harding, S. E.; Rowe, A. J.; Harton, J. C. *Analytic Ultracentrifugation in Biochemistry and Polymer Science*; The Royal Society for Chemistry: Cambridge, 1992). Solution densities were estimated using solute concentration-dependent density tables in the CRC Handbook of Chemistry and Physics. The data were fit as single species to provide an estimate of the aggregation states. Curve fitting of analytical ultracentrifuge data was done using Igor Pro (Wavemetrics Inc., Oswego WS) with procedures adapted from Brooks et al. (Brooks, I. S.; Soneson, K. K.; Hensley, P. *Biophys. J.* 1993, 64, 244) by Dr. James D. Lear.

Circular Dichroism (CD) Analysis. CD spectra were recorded on an Aviv 62DS spectropolarimeter (Lakewood, N.J.) in PBS buffer, pH 7.4. All peptide concentrations were determined by amino acid analysis of a stock solution (5 mg/ml). Experiments were performed in a rectangular cell with pathlength of 1 cm for low concentration samples and pathlength of 1 mm for high concentration samples. Spectra were scanned from 250 nm to 200 nm with data taken every 1 nm. The temperature of the solution was maintained by a thermostatically controlled cuvette holder (HP model 89101A). Temperature scans were performed from 0° C. to 100° C. in 1° C. steps. Three scans were performed on a single sample and averaged. Each data point was collected after 30 seconds of thermal equilibration at the desired temperature. Urea titration scans were performed manually starting with the 8 M concentrated sample followed by serial dilution to the desired urea concentration. At each concentration, the sample was allowed to equilibrate for 5 min before recording the CD signal.

The analysis of CD thermal melting data was performed according to a previously described procedure using a two-state model (Schneider, J. P.; Lear, J. D.; DeGrado, W. F. *J. Am. Chem. Soc.* 1997, 119, 5742-5743). Temperature-dependent ellipticity data for each protein at different concentrations were fitted globally using a non-linear least-squares fitting procedure supplied with the Origin 6.0 software. For wild-type A1, the concentrations used for curve fitting were 10 and 100 µM, while 2 and 100 µm were used to fit data for the 92% fluorinated A1. The thermodynamic quantities $T_m$, $\Delta H_m$, $\Delta C_p$ and $K_d$ were parameters of the fitting procedure and are reported in the 1 M standard state. The free energy of folding at any temperature is given by equation 1.

$$\Delta G° = \Delta H_m(1-T/T_m) - \Delta C_p((T_m-T)+T\ln(T/T_m)) \quad (1)$$

EXAMPLE 5

The following Example provides interpretation of results of the biochemical analyses of wild type GCN4-p1 peptide and the corresponding artificial Tfl-GCN4-p1 peptide in which the four leucines were replaced with non-natural amino acids.

Figure 2A:
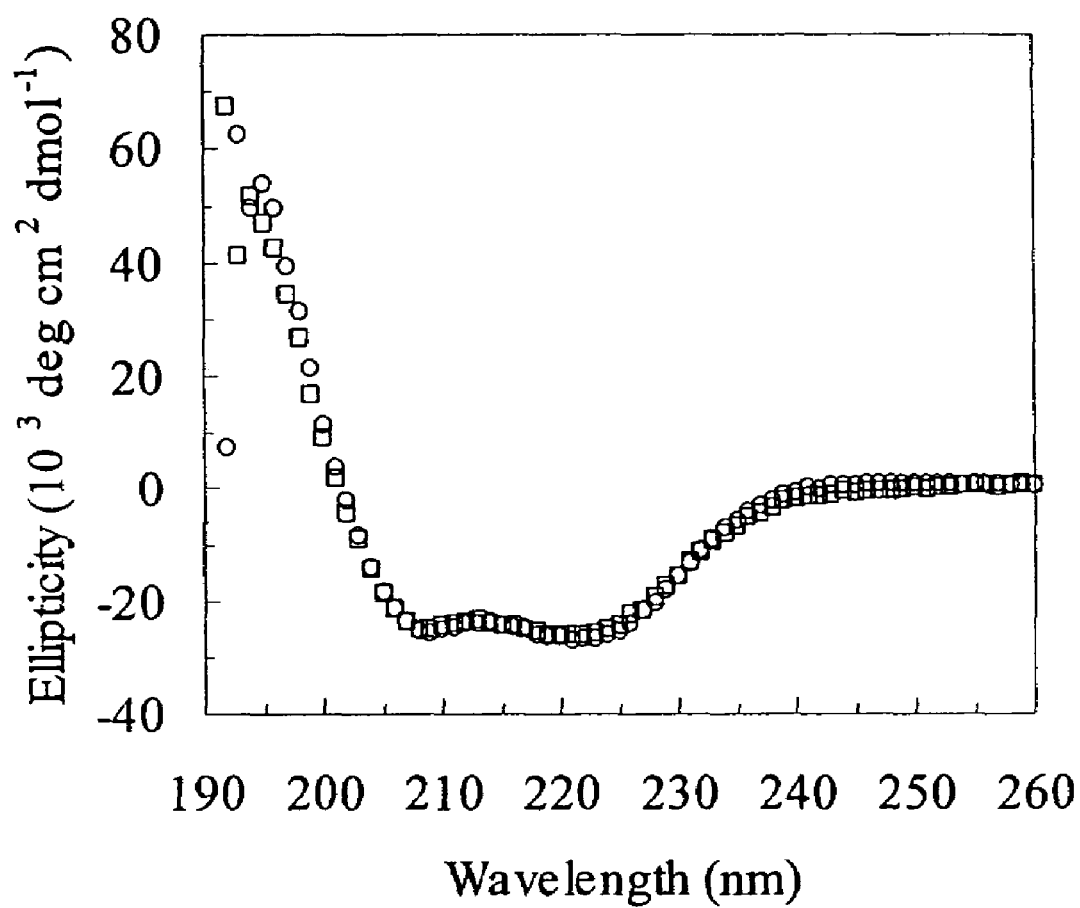
FIG. 2a shows CD spectra of Leu-GCN4-p1 (□) and Tfl-GCN4-p1 (○) at 0° C. and 30 μM.

Secondary structures of wild type polypeptide Leu-GCN4-p1 and the corresponding artificial polypeptide Tfl-GCN4-p1 were analyzed by circular dichroism (CD). The CD spectra of both peptides indicated high helical content as evidenced by double minima at 222 nm and 208 nm (FIG. 2A). The spectra of the wild type and fluorinated peptides are essentially coincident, suggesting nearly identical secondary structures; both peptides are highly helical at 0° C. This confirms the proposal that replacement of leucine with Tfl would not disrupt interhelical packing and interfere with folding of the coiled-coil structure. Ultracentrifugation indicated that Tfl-GCN4-p1 is predominantly dimeric at the concentrations of interest in this work. Data for Tfl-GCN4-p1 were fit to a monomer-dimer-trimer equilibrium, giving values of $K_d$'s the order of $10^{-8}$ M and $10^{-14}$ $M^2$, respectively, for the monomer-to-dimer and monomer-to-trimer equilibria. In the concentration range of approximately 10 µM-40 µM the protein is approximately 85% dimeric.

Figure 2B:
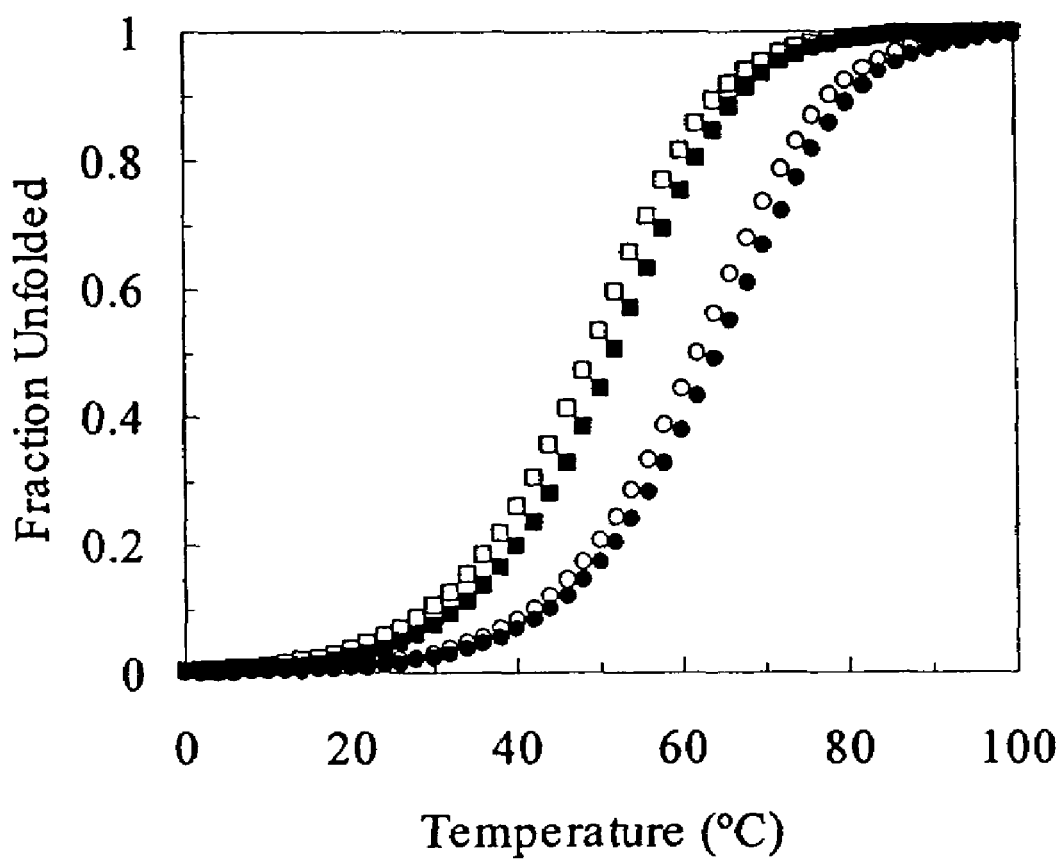
FIG. 2b shows thermal unfolding profiles for Leu-GCN4-p1 (squares) and Tfl-GCN4-p1 (circles) at 30 μM (open symbols) and 85 μM (close symbols).
Figure 2C:
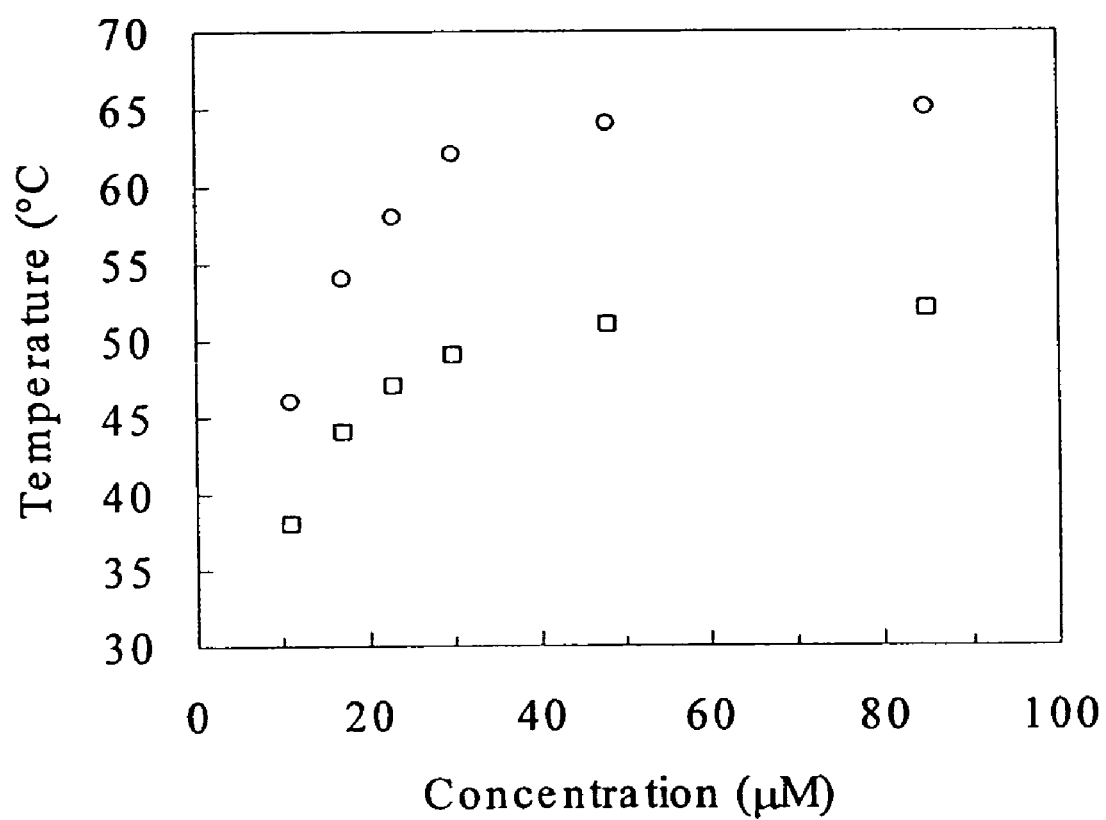
FIG. 2c shows concentration dependence of thermal melting temperature of Leu-GCN4-p1 (□) and Tfl-GCN4-p1 (○).

The thermal stabilities of the coiled-coil dimers of Leu-GCN4-p1 and Tfl-GCN4-p1 were examined by CD spectroscopy (FIG. 2B). A significant increase in the thermal stability of Tfl-GCN4-p1 as compared to Leu-GCN4-p1 is reflected in an elevation of the thermal denaturation temperature from 48° C. to 61° C. The 13° C. increase in $T_m$ is remarkable in view of the fact that no increase in the thermal stability of GCN4- p1 has been reported based solely on substitution of the leucine residues at the d-positions. Mutations at the d-positions to other natural amino acids have all resulted in losses in helix stability due to decreases in packing efficiency since such changes are usually of the "large to small" type (J. Moitra, L. Szilak, D. Krylov, C. Vinson, *Biochemistry* 36, 12567, 1997). The similarity in the melting curves of the two peptides suggests similarly cooperative unfolding of the dimeric structure to unfolded monomers. As expected for a monomer-dimer equilibrium, the denaturation curves depend on the peptide concentrations, and their midpoints shift to higher temperature as the concentrations of peptides are increased (FIG. 2C). The thermodynamic changes associated with the transition (folded dimer to unfolded monomers) is calculated from the melting curves by fitting the data to a monomer-dimer equilibrium (J. P. Schneider, J. D. Lear and W. F. DeGrado, *J. Am. Chem. Soc.* 119, 5742, 1997). Global analysis of the thermal unfolding curves at two different concentrations, approximately 85 µM and 3 µM, gave a calculated $\Delta H°$ of 60.2 kcal mol$^{-1}$, $T_m$ of 385.4 K and $\Delta C_p$ of 530 cal mol$^{-1}$ K$^{-1}$ for Tfl-GCN4-p1 (1 M standard state); the corresponding values for Leu-GCN4-p1 are 70.3 kcal mol$^{-1}$, 365.6 K and 740 cal mol$^{-1}$ K$^{-1}$ respectively. Under all conditions where a direct experimental comparison was possible, Tfl-GCN4-p1 was 0.5~1.2 kcal mol$^{-1}$ more stable than Leu-GCN4-p1; for example, at 50° C., the $K_d$ of dimerization was 67.8 µM for Leu-GCN4-p1 and 9.8 µM for Tfl-GCN4-p1.

Figure 2D:
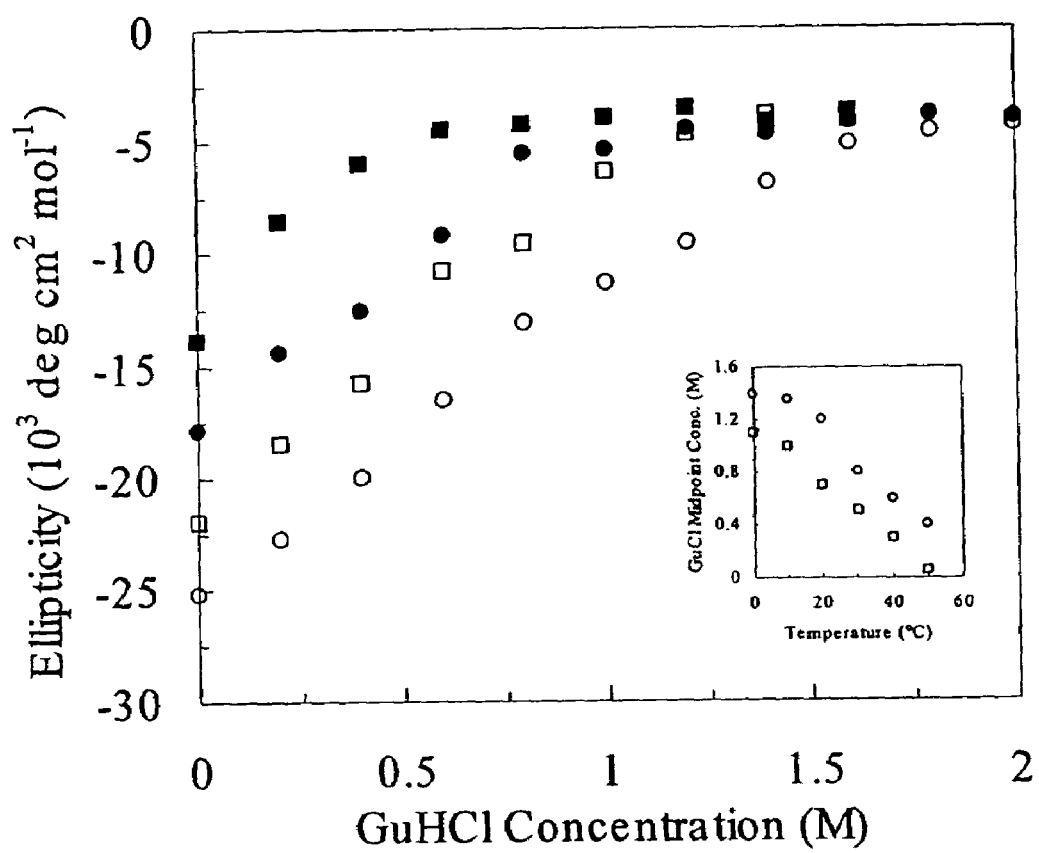
FIG. 2d shows Guanidinium hydrochloride (GuHCl) titration of Leu-GCN4-p1 (squares) and Tfl-GCN4-p1 (circles). The difference in the ability to these molecules to resist denaturation is examined at 30° C. (open symbols) and 50° C. (closed symbols). The ellipticity is monitored at 222 nm and with a peptide concentration of 30 μM. Insert: GuHCl titration midpoint concentration, as defined by the concentration of GuHCl that is needed to denature 50% of the peptides, are plotted as a function of temperature, as described in Examples 5.

The stability of Tfl-GCN4-p1 toward denaturation by chaotropic reagents was demonstrated through guanidine hydrochloride (GuHCl) titration experiments (FIG. 2D). At each temperature examined, the fluorinated peptide displayed significantly lower susceptibility toward denaturation by of GuHCl: in each case, the concentration of GuHCl needed to unfold 50% of the peptide was higher for Tfl-GCN4-p1 than that for the wild-type peptide.

To determine the origins of the stabilizing effect of side-chain fluorination, molecular dynamics (MD) calculations were performed using the Poisson-Boltzmann (PB) continuum description of the solvent (K. T. Lim, S. Brunett, M. Iotov, B. McClurg, N. Vaidehi, S. Dasgupta, S. Taylor, and W. A. Goddard III, *J. Comp. Chem.* 18, 501, 1997) which includes the Cell Multipole Method (H. Q. Ding, N. Karasawa, W. A. Goddard III, *J. Chem. Phys.* 97, 4309, 1992; D. J. Tannor, B. Marten, R. Murphy, R. A. Friesner, D. Sitkoff, A. Nicholls, M. Ringnalda, W. A. Goddard III, *J. Am. Chem. Soc.*, 116, 11875, 1994; A. Ghosh, C. S. Rapp, R. A. Friesner, *J. Phys. Chem. B*, 102, 10983, 1998; D. J. Tannor, B. Marten, R. Murphy, R. A. Friesner, D. Sitkoff, A. Nicholls, M. Ringnalda, W. A. Goddard III, *J. Am. Chem. Soc.*, 116, 11875, 1994; A. Ghosh, C. S. Rapp, R. A. Friesner, *J. Phys. Chem. B*, 102, 10983, 1998). The PB description of solvation implicitly includes entropic changes in the solvent, thus the calculations lead directly to the binding free energies ($\Delta G^{BE}$). The MPSIM MD program and the DREIDING Force Field (FF) were used for all calculations.

The starting structure for the Leu-GCN4-p1 dimer was taken from the RCSB Protein Data Bank; those of the fluorinated dimers were derived from the native dimer structure by replacement of the appropriate methyl hydrogens with fluorines, followed by re-optimization of the structure. Because the γ-carbon of Tfl is asymmetric (FIG. 1B), multiple arrangements of adjacent diastereotopic trifluoromethyl groups had to be considered.

When both Tfl residues at a given d-position are of the (2S,4S) configuration, the two trifluoromethyl groups are relatively close to one another; the fluorinated carbon centers are separated by ca. 6 Å. On the other hand, when two (2S,4R) isomers are juxtaposed, the corresponding carbon-carbon distance increases to about 8 Å. In the remaining configurations (where the two strands carry different isomers), the trifluoromethyl groups are separated by intermediate distances.

To determine how side-chain stereochemistry affects dimer stability, simulations were performed on all configurations. For simulation of strands containing different stereoisomers of Tfl, only those cases in which all four Tfl on one strand have the same stereoconfiguration were considered.

From the 1 ns trajectory, the average properties were calculated over 800 ps after equilibration. $\Delta G^{BE}$ was calculated as the difference in energies of the solvated dimer and the corresponding solvated monomers. Table 1 reports the average values of $\Delta G^{BE}$ (per monomer) for the native and fluorinated forms. $\Delta G^{BE}$ is the difference in energy (averaged over 800 ps of MD after equilibration) of solvated monomers and the solvated dimer each from separate SGB MD calculations (final solvation energies with PBF). $\Delta G^{BE}$ is quoted per mole of the monomer. % increase is the increase in $\Delta G^{BE}$ compared to the Leu-GCN4-p1 structure. Also shown is the % helicity of each.

TABLE 1

Binding free energies ($\Delta G^{BE}$, kcal/mol) of Leu-GCN4-p1 and fluorinated dimers.

| Structure | $\Delta G^{BE}$ | % increase | % helicity[b] |
|---|---|---|---|
| Leu-GCN4-p1 | 65.08 | 0 | 90.8 |
| [a]Close (4S, 4S) | 93.75 | 44 | 84.3 |
| Far (4R, 4R) | 98.14 | 51 | 79.4 |
| Mixed (4S, 4R) | 99.20 | 52 | 81.1 |
| Mixed (4R, 4S) | 111.15 | 71 | 89.3 |
| Tfl-average | 100.56 | 55 | 83.5 |
| Hfl-GCN4-1p | 77.21 | 19 | 78.5 |

[a]Close Far, Mixed: Configuration of the pair of trifluoromethyl groups as illustrated in FIG 4.
Tfl-average: The averaged $\Delta G^{BE}$ of the four configurations.

[b]Helicity quoted here was calculated as the ratio of the residues with torsion angles φ and Ψ in the helical region of the Ramachandran plot to the total number of residues in the protein.

The Tfl-GCN4-p1 dimers are predicted to exhibit $\Delta G^{BE}$ ca. 55% larger than that of the leucine form (calculated relative to the respective random coil monomers). The various stereochemical arrangements lead to increases in binding energies ranging from 44% to 71%, indicating that side-chain configuration may have some differential effect on dimer stability. Similar calculations for the hexafluoroleucine (Hfl) dimer leads to the prediction that such dimers will be significantly less stable than the Tfl dimers but marginally more stable (19%) than the wild type.

To investigate the source of stability of the fluorinated dimers, the components of the binding energy for each peptide were analyzed (Table 2). The primary driving forces for stabilizing the Tfl-GCN4-p1 dimers arise from van der Waals (vdW) and hydrogen bonding interactions. The solution structures of Hfl and wild type monomers are globular, while the Tfl-GCN4-p1 monomer is more extended. This is due to the Tfl side chains, which produces local "kinks" due to favorable electrostatic interactions. These "kinks" stabilize the more extended form for the monomer of Tfl-GCN4-p1. For example a hairpin is formed from favorable interactions between $Tfl_5$ and $Tfl_{12}$ in the monomer of Tfl-GCN4-p1. The wild type and Hfl monomers, on the other hand, do not form local "kinks" but instead fold into globular structures. These structures have more non-local hydrogen bonds and more favorable vdW contacts than the more extended Tfl-GCN4-p1 monomer. Hence, the gain in H-bond and vdW energies in forming a dimer is greater for Tfl-GCN4-p1 than for the wild-type or Hfl peptides because the latter peptides must pay an energy cost to unfold before dimerization.

TABLE 2

Components of $\Delta G^{BE}$ (kcal/mol) for Leu-GCN4-p1 and fluorinated dimers (quoted for one mole of the monomer)

| Structure | $\Delta G^{valence}$ | $\Delta G^{coulomb+solvation}$ | $\Delta G^{vdW}$ | $\Delta G^{Hbond}$ |
|---|---|---|---|---|
| Leu-GCN4-p1 | −16.12 | −16.66 | 41.82 | 56.05 |
| [a]Close (4S, 4S) | −8.46 | −16.64 | 59.56 | 59.29 |
| Far (4R, 4R) | −9.54 | +1.73 | 42.16 | 63.80 |
| Mixed1 (4S, 4R) | −5.36 | −10.55 | 65.17 | 49.94 |
| Mixed2 (4R, 4S) | −27.96 | −1.79 | 48.29 | 92.61 |
| Tfl-average | −12.83 | −6.82 | 53.80 | 66.41 |
| Hfl-GCN4-p1 | −23.06 | 7.24 | 36.51 | 56.19 |

[a]Close Far, Mixed: Configuration of the pair of trifluoromethyl groups as illustrated in FIG 4.
Tfl-average: The averaged $\Delta G$ of the four configurations.

Consideration of electrostatic (intra- and inter-peptide coulomb forces) and solvation interactions suggests that the hydrophobic preference in the dimer for burial of $CF_3$ is greater than for $CH_3$. Considering just coulomb and solvation interactions, the driving force for dimerization is predicted to decrease in the order Hfl>Tfl>Leu. It is the balance of desolvation, electrostatics, H-bonding and vdW forces that leads to the prediction that the Tfl dimers are more stable than the Hfl dimer, which in turn is more stable than the native leucine dimer. The average helicity of dimers is predicted to be 90.8% for Leu-GCN4-p1, 83.5% for Tfl, and 78.5% for Hfl.

These results demonstrate that the subtle change from four leucine methyl groups to four trifluoromethyl groups results in a large gain in stability of the folded structure. It is remarkable that for a small peptide of the size of GCN4-p1, fluorination results in a modified coiled-coil structure that is highly resistant to both thermal and denaturant unfolding as compared to the wild-type peptide.

EXAMPLE 6

The following example describes biochemical analysis of wild type bZip peptide peptide and the corresponding artificial bZip peptide in which the leucines were replaced with non-natural amino acids.

To investigate the effects of fluorination on the biological activities of coiled-coil proteins, a fluorinated DNA binding protein Tfl-bZip was constructed. The wild-type protein Leu-bZip is a 56 amino acid segment (residues 226-281) of the eukaryotic transcription factor GCN4. The N terminus of Leu-bZip contains the DNA recognition domain that is rich in basic residues such as lysine and arginine. The C-terminus subdomain of Leu-bZip contains the GCN4-p1 peptide segment and facilitates the dimerization of the protein. While the direct contact between the N terminus residues with DNA is important to the recognition between protein and DNA, the specific protein-protein interactions at the C terminus are also responsible for the specificity and affinity between protein and DNA (K. Arndt and G. R. Fink, Proc. Natl. Acad. Sci. USA, 83, 8516, 1986; Y. Aizawa, Y. Sugiura, M. Ueno, Y. Mori, K. Imoto, K. Makino and T. Morii, Biochemistry 38, 4008, 1999; S. C. Hockings, J. D. Kahn and D. M. Crothers, Proc. Natl. Acad. Sci. USA 95, 1410, 1998). Tfl-bZip contains Tfl-GCN4-p1 at its dimerization domain while the DNA binding domain is unchanged. The secondary structures of the two proteins were identical as confirmed by CD and the thermal melting temperature of the Tfl-bZip was elevated by 8° C. compared to Leu-bZip at 10 µM protein concentration.

Figure 3A:
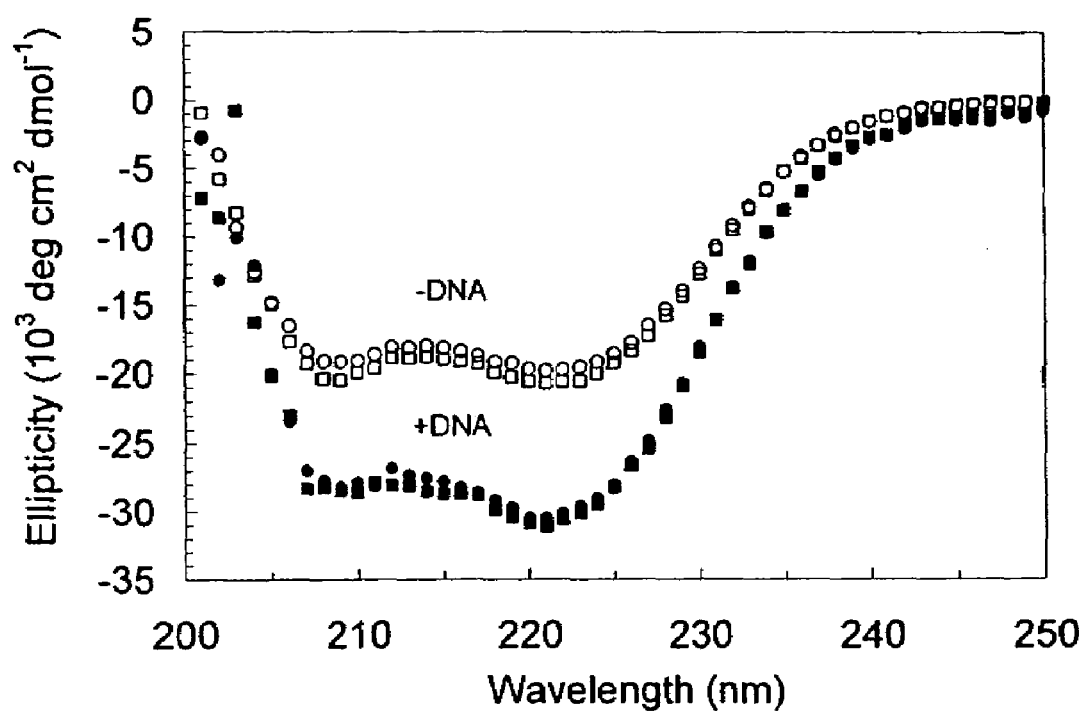
FIG. 3a shows CD spectra for Leu-bZip (squares) and Tfl-bZip (circles) without CREB DNA binding sequence (open symbols) and with DNA (closed symbols) at 0° C., as described in Example 6.

The DNA binding domain of Leu-bZip is in a random coil conformation in the absence of specific DNA sequences, while the dimerization domain forms a dimeric coiled coil through the leucine zipper motif at concentrations above the monomer-to-dimer equilibrium (M. A. Weiss, T. Ellenberger, C. R. Wobbe, J. P. Lee, S. C. Harrison and K. Struhl, Nature 346, 575, 1990). Upon recognition of DNA, the DNA binding region folds into an α-helical structure and the protein binds to the DNA in a "chopstick" model (T. Ellenberger, C. J. Brandl, K. Struhl and S. C. Harrison, Cell 71, 1223, 1992; P. Konig and T. J. Richmond, J. Mol. Biol. 233, 139, 1993; W. Keller, P. Konig and T. J. Richmond, J. Mol. Biol. 254, 657, 1995). CD analysis of the Tfl-bZip secondary structure revealed that the fluorinated protein behaves the same way as Leu-bZip (FIG. 3A). Before the addition of oligonucleotides containing the CREB binding site, Tfl-bZip is approximately 70% helical, corresponding to its helical dimerization domain. After the addition of oligonucleotides, Tfl-bZip turned into almost 100% α-helical, indicating a transition of the binding region from coil to helix after DNA recognition. The similar change in protein structure observed for Leu-bZip and Tfl-bZip confirms that the fluorination of the zipper domain does not affect the recognition and association between protein and DNA.

Figure 3B:
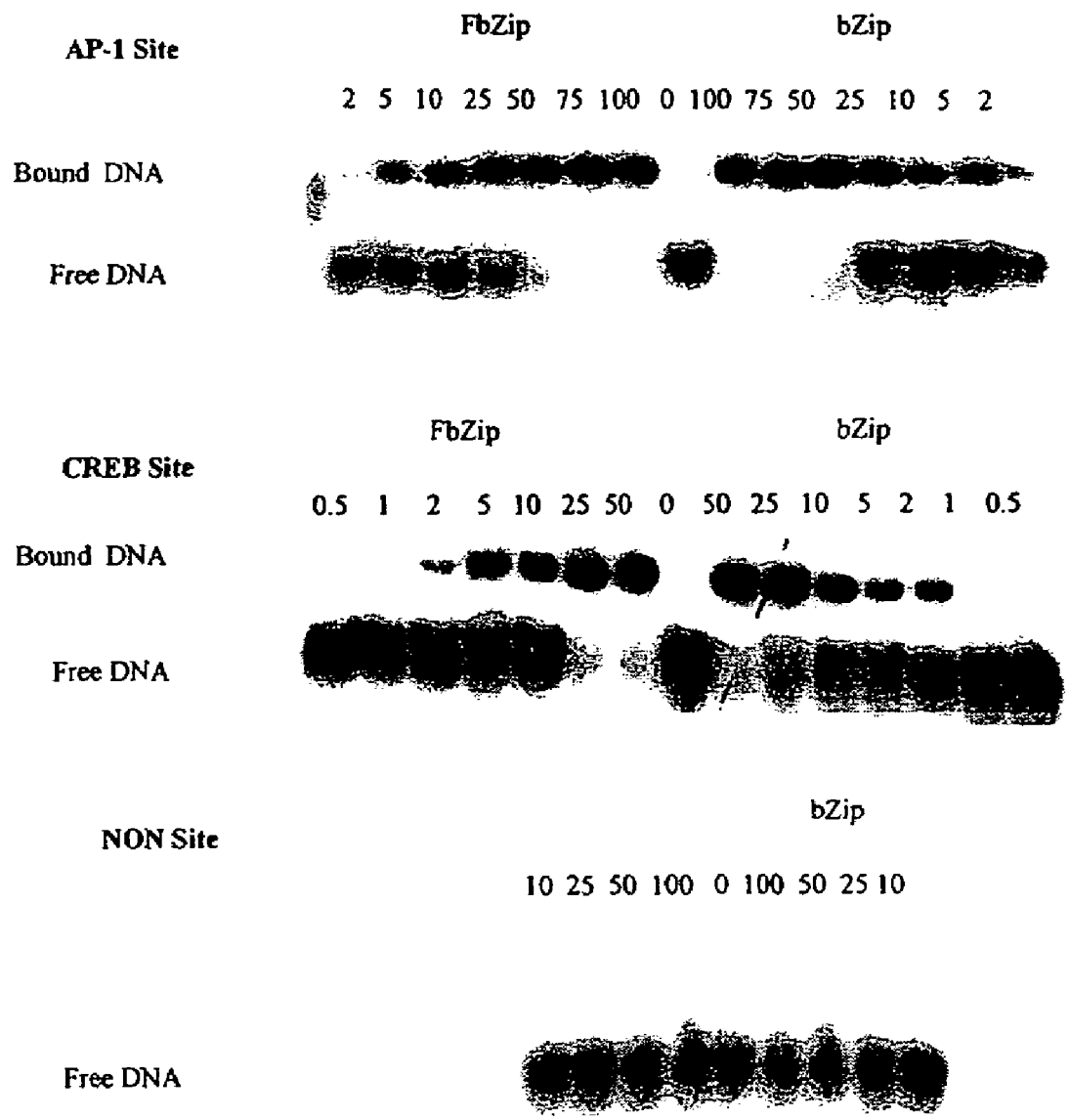
FIG. 3b shows mobility shift assay of Leu-bZip and Tfl-bZip binding to oligonucleotides containing the AP-1 binding site (5'-GTGGAGATGACTCATCTCCGG-3', top), the CREB binding site (5'-TGGAGATGACGTCATCTCCT-3', middle) and the nonspecific sequence (NON, 5'-GATCCCAACACGTGTTGGGATC-3', bottom), as described in Example 6.

The affinity and specificity of the fluorinated protein binding to recognition sequences were shown to be identical to the wild type protein by gel-retardation assays (S. J. Metallo and A. Schepartz, Chem. Biol. 1, 143, 1994;. D. N. Paolella, C. R. Palmer and A. Schepartz, Science 264, 1130, 1994). (FIG. 3B) Leu-bZip binds to both the AP-1 and CREB binding sites with equal affinities even though the spacing between the half-sites of DNA is different. Densitometry analysis of the mobility shift assay revealed that Tfl-bZip binds to both sequences with equal specificity ($K_d$=12.5±0.7 nM for AP-1 and 5.4±0.6 nM for CREB) and identical affinity compared to that observed for Leu-bZip (Kd=12.8±1 nM for AP-1 and 4.8±0.5 nM). Neither protein recognizes nonspecific (NON) sequences as shown by the lack of protein-bound DNA in the assay containing NON oligonucleotides.

EXAMPLE 7

The following example describes biochemical analysis of wild type A1 peptide and the corresponding artificial peptide of the invention in which the leucines were replaced with non-natural amino acids.

The A1 protein (FIG. 4A) forms dimeric coiled coils in aqueous solution. It has been previously used as an element of artificial multidomain proteins that form reversible hydrogels under conditions of controlled pH and temperature (Petka, W. A.; Harden, J. L.; McGrath, K. P.; Wirtz, D.; Tirrell, D. A. Science 1998, 281, 389-392). The A1 protein contains eight leucine residues, of which six are distributed at the d positions of the six heptad repeats. By using a leucine auxotrophic strain of E. coli, trifluoroleucine-substituted A1 was prepared at levels of fluorination that ranged from 17% to 92%. The thermal and chemical stabilities of the fluorinated proteins were significantly elevated compared to those of the wide type A1 protein. Hfl does not support measurable protein synthesis in *E. coli* under the conditions examined in this example.

The ability of Tfl to support protein synthesis is shown in FIG. 4B. The increase in cell density three hours after the cells were suspended in medium enriched with Tfl shows that the incorporation of Tfl into essential cellular proteins produced after the medium shift step are functional to continually support cell growth. This is consistent with the observation that Tfl can support the exponential phase of cell growth (Rennert, O. M.; Anker, H. S. *Biochemistry* 1963, 2, 471).

Figure 5:
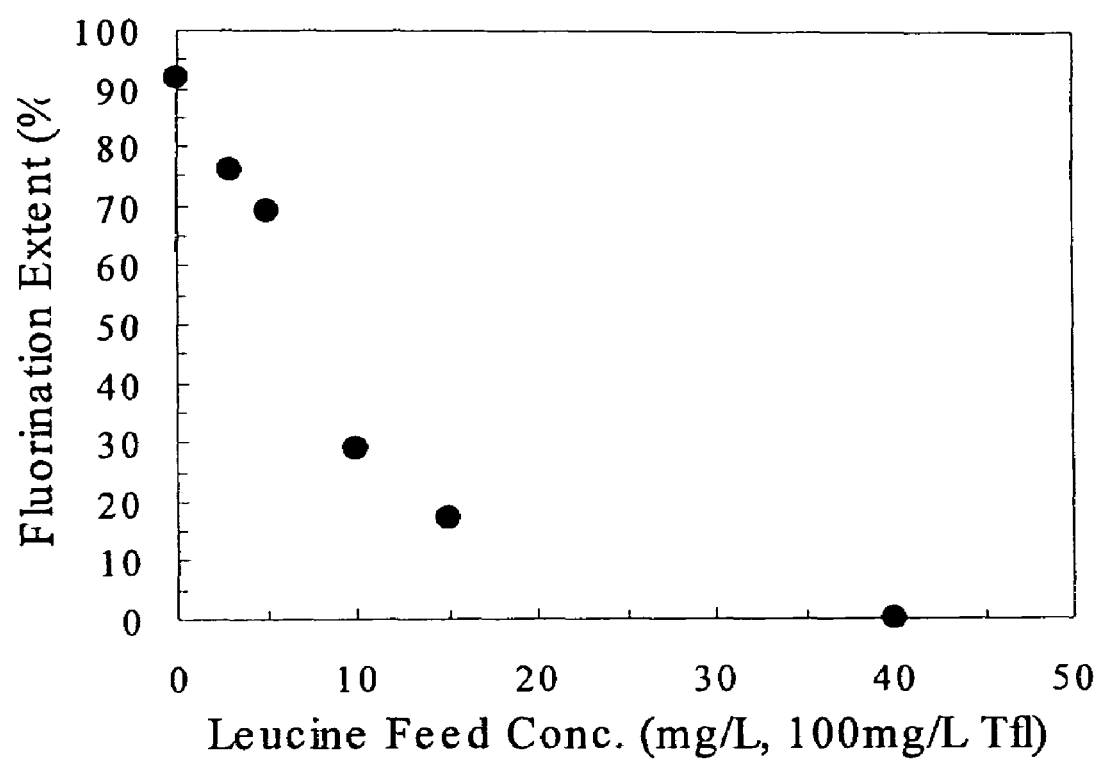
FIG. 5 shows the results of varying the concentration of leucine in the expression medium while holding the concentration of trifluoroleucine constant at 100 mg/L on the extent of fluorination in A1, as described in Example 7. Normal leucine concentration in expression medium is 40 mg/L. The extent of incorporation is determined by amino acid analysis.

The ability to control the level of substitution of non-natural amino acids for natural amino acid counterparts is demonstrated in FIG. 5. The degree of substitution is determined through the diminution of leucine mole fractions from amino acid analysis (AAA). MALDI mass spectrometry analysis was also performed on the protein. It was evident for FA1-92, the predominant peak observed was 8736 mass units, corresponding to 8 substitutions of trifluoromethyl groups over methyl groups (each substitution results in increase of 54 mass units). However, the peak was broad, indicating the presence of proteins that were not completely substituted, as confirmed by the 92% replacement by amino acid analysis. 100% replacement was not obtained in the absence of leucine in the expression medium possibly due to the trace amount of leucines resulting from cellular protein degradation. The levels of incorporation could be related to the amounts of leucine in the expression medium in a predictable fashion. It can be estimated that at 50% substitution can be achieved at a leucine (pure L form) concentration of 8 mg/L (50 µM) and Tfl (DL mixture) concentration of 100 mg/L (540 µM), which suggests that specificity of Tfl for LeuRS is only reduced five times when compared to leucine.

Figure 6:
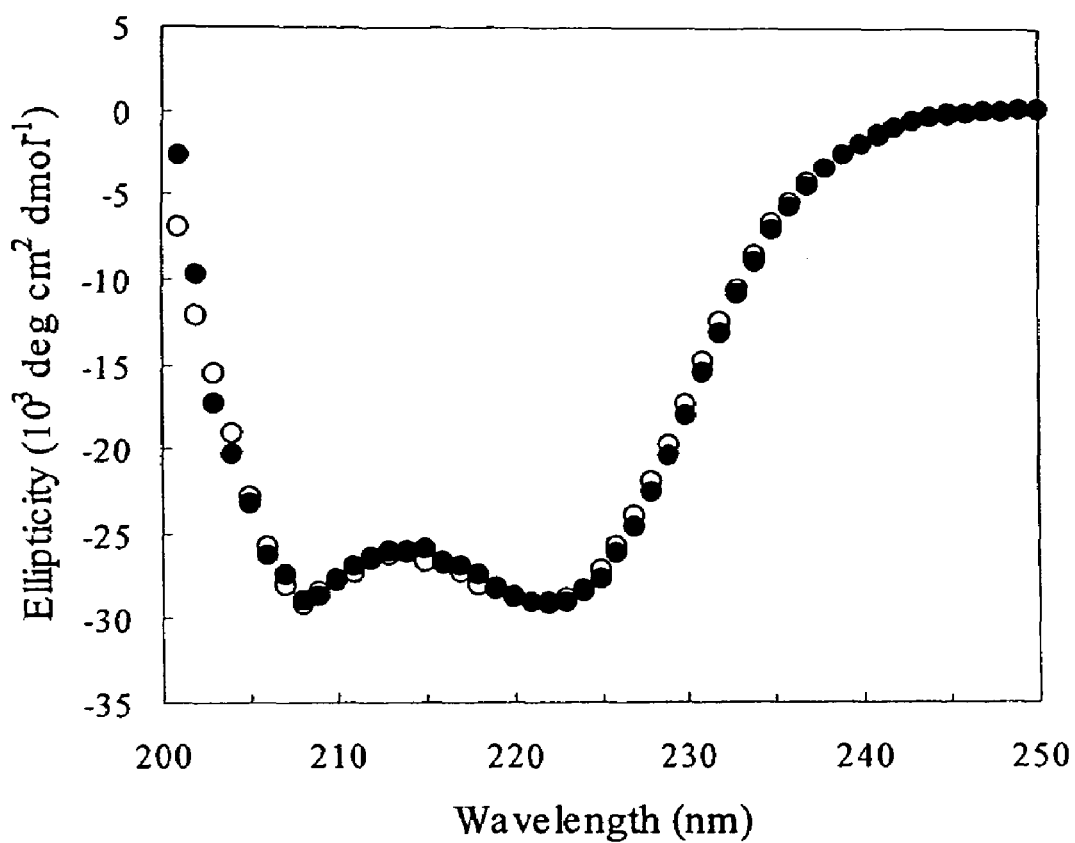
FIG. 6 shows CD spectra of A1 (●) and FA1-92 (○) at 0° C. (10 μM protein concentration, PBS buffer, pH 7.4) as described in Example 7. Both proteins are highly helical as suggested by the ellipticity at 222 nm. The overlap of the spectra indicates identical secondary structures.

The overall secondary structures of A1-WT and FA1-92 are essentially identical with the same maximum helicity as shown in FIG. 6. This is essentially due to the fact that Tfl is able to maintain the tightly packaged protein core.

Figure 7:
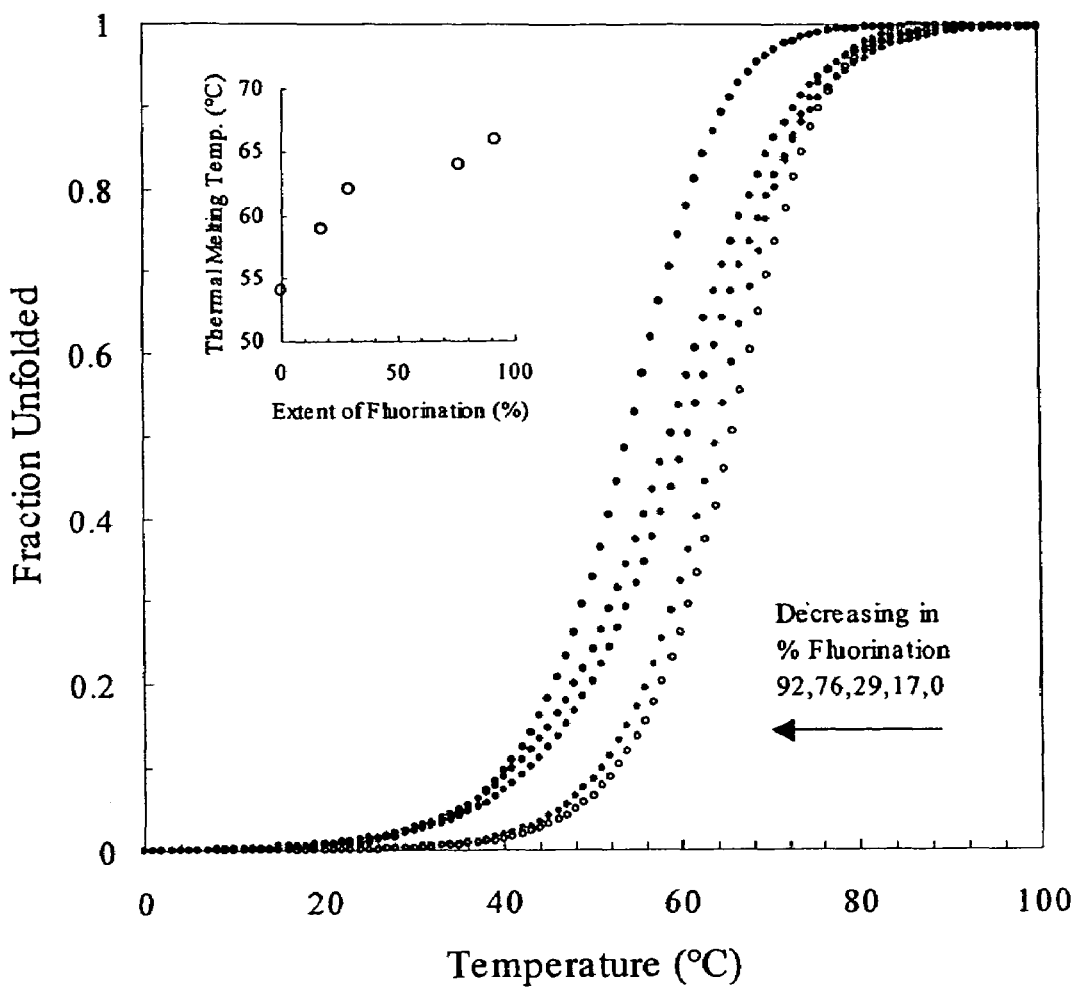
FIG. 7 shows the results of a thermal denaturing experiment on fluorinated A1 proteins with different level of Tfl incorporation as described in Example 7. Insert: The thermal melting temperature ($T_m$) plotted as a function of level of incorporation. $T_m$ is defined as the temperature at which 50% of the peptide has unfolded. The stability of the protein increases with increasing level of 2trifluoroleucine substitution. (10 μM protein concentration, PBS buffer, pH 7.4).
Figure 8:
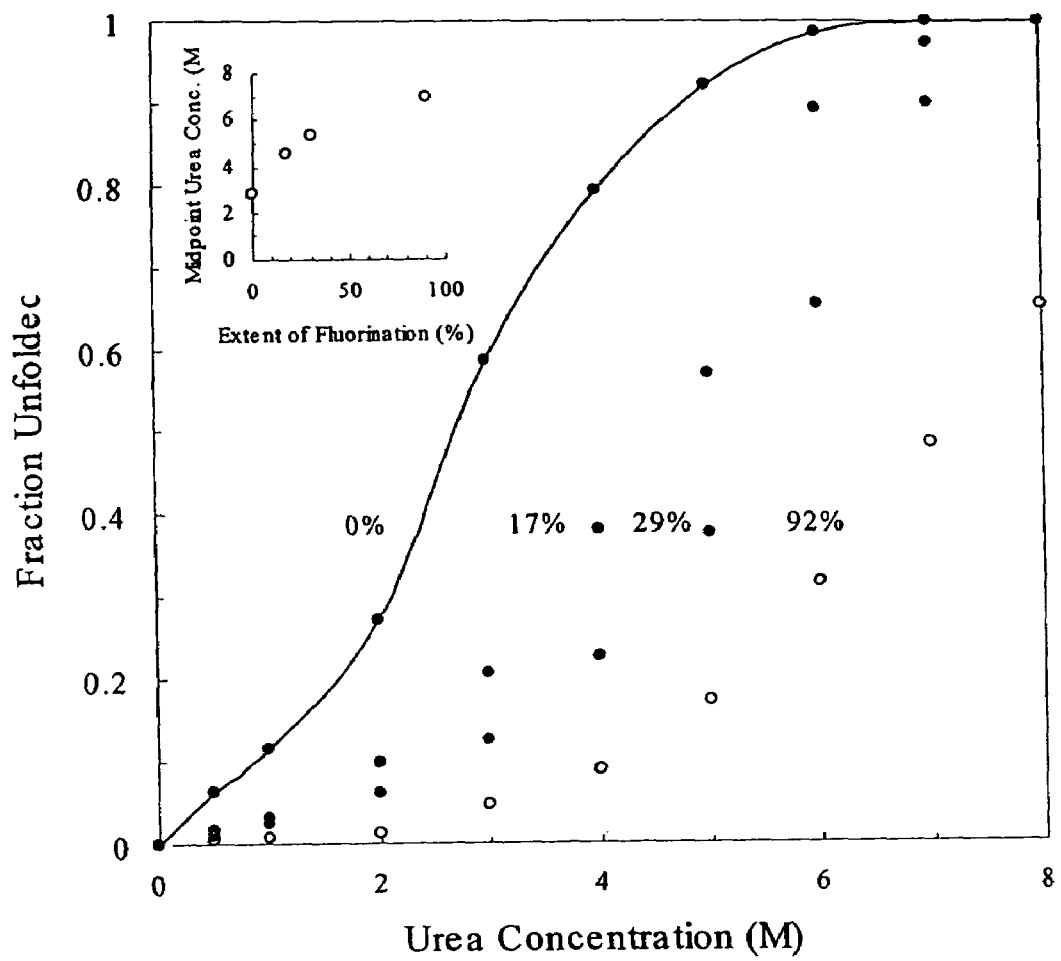
FIG. 8 shows the results of urea titration of A1 and fluorinated A1 at 0° C. demonstrating that the chemical stability is also improved upon Tfl incorporation as shown in Example 7.

Thermal and chemical unfolding studies revealed that the fluorinated peptides FA1-92, FA1-17, and FA1-29 are highly resistant to both thermal and chemical denaturation. The $T_m$ of the fully FA1-92 was elevated by 13° C. compared to A1-WT (FIG. 7, Table 3), while $C_m$ for FA1-92 was increased to 7 M from the measured 2.7 M for A1-WT (FIG. 8, Table 3). These elevations are significant for a protein complex of 8 kDa size. More surprisingly, proteins with low levels of fluorination (FA1-17 and FA1-29) produced the most pronounced increase in stability. This is striking because at 17% substitution rate, of the six leucine residues folded at the helical interface, only one is replaced by 2 on average. However, the single substitution of methyl with trifluoromethyl resulted in increases of $T_m$ by 6° C. and $C_m$ by approximately 2 M. This result is contrary to the initial proposal that fully fluorinated proteins are the most stable because fluorocarbons self-aggregate more strongly in water than hydrocarbons. These results suggest that introduction of only a few trifluoromethyl groups into a core of hydrocarbons is sufficient to raise the protein folding driving force significantly. This result has important ramifications for using Tfl in the engineering of more stable protein structures.

TABLE 3

| Protein | $T_m^a$ (10 µM) | $T_m^b$ (1M) | $\Delta G°$ (37° C.)[c] | $\Delta\Delta G°$ | $\Delta H_m^d$ (1M) | $\Delta C_p^e$ (1M) | $C_{urea, 50\%}^f$ (0° C.) |
|---|---|---|---|---|---|---|---|
| A1-WT | 54 | 103 | −10.7 | | −70.9 | −252 | 2.8 |
| FA1-92 | 67 | 116 | −13.1 | −2.4 | −77.0 | −272 | 7 |

[a]The midpoint of the thermal denaturation curve at 10 µM protein concentration (PBS, pH 7.4). Units for $T_m$ are ° C.
[b]Midpoint of the thermal denaturation curve extrapolated to 1M standard state using non-linear least square fit.
[c]The free energy of folding at 37° C. at 1M standard state. Units for $\Delta G°$ and $\Delta\Delta G°$ are kcal/mol.
[d]The enthalpy of folding at the midpoint temperature extrapolated to 1M standard state, units are in kcal/mol.
[e]Heat capacity change upon folding at 1M standard state, units are in cal/mol-K. The uncertainties for $T_m$ (1M), $\Delta G°$, $\Delta H_m$ and $\Delta C_p$ are ± 1.5° C., 1.2, 4.8 kcal/mol, and 120 cal/mol-K, respectively.
[f]The midpoint urea denaturation concentration at 0° C. in M of urea.

Global thermodynamic fitting was used to obtain the thermodynamic quantities associated with the monomer to dimer transition for A1-WT and FA1-92. The intermediate level fluorinated proteins, FA1-17 and FA1-29 were not fitted using the procedure because the heterogeneity of the samples would not be described accurately by the two-state model. The presence of a heterogeneous population can be seen from the broadening of the thermal melting curves at substitution rates of 17 and 29%. However, even for the nearly completely substituted FA1-92, the protein sample was still a mixed population because Tfl was used as an equal molar mixture of (2S, 4S) and (2S, 4R) diastereomers. The free energy of unfolding for FA1-92 was 2.4 kcal/mol more favorable than A1-WT at 37° C., which corresponded to 0.4 kcal/mol of stabilizing energy per Tfl molecule involved at the helix interface. Considering the large number of leucines packed in the hydrophobic core of proteins, the additive stabilizing effects of Tfl can be quite substantial.

These results demonstrate that it is possible to efficiently incorporate Tfl into proteins produced in vivo, control Tfl incorporation ratio, maintain protein secondary and higher order structures and elevate the resistance of the proteins to thermal and chemical denaturation. Since leucine is the most abundant abundance of the amino acids in cellular proteins (9%) (T. Creighton, *Proteins: Structure and Molecular Properties* (W. H. Freeman and Company, New York, 1997) and is especially important in determining the structure and stability of helix-bundle and other hydrophobic structural motifs. These results indicate the methods of the invention should apply to any protein with a hydrophobic core. In addition, since fluorination results in minimal modifications to protein structure and core packing, it is complementary to other existing technologies used in elevating protein stability (Lee, B.; Vasmatzis, G. *Curr. Opin. Biotech.* 1997, 8, 423-426. b. Handel, T. M.; Williams, S. A. DeGrado, W. F. *Science*, 1993, 261, 879-885. c. Mer, G.; Hietter, H.; Lefevre, J. F. *Nat. Struct. Biol.* 1996, 3, 45-53. d. Zhang, X, J.; Baase, W. A.; Schoichet, B. K.; Wilson, K. P.; Matthews, B. W. *Protein Eng.* 1995, 8, 1017-1022). Therefore, fluorination can be used as a final "push" in protein stabilization after other methods such as directed evolution (Arnold, F. *Chem. Eng. Sci.* 1996, 51, 5091-5102; Giver, L.; Gershenson, A.; Freskgard. P. O.; Arnold, F. H. *Proc. Natl. Acad. Sci. USA* 1998, 95, 12809-12813; Zhou, Y, F.; Bowie, J. U. *J. Biol. Chem.* 2000, 275, 6975-6979) or rational design (DeGrado, W. F.; Summa, C. M.; Pavone, V.; Nastri, F.; Lombardi, A. *Annu. Rev. Biochem.* 1999, 68, 779-819; Dahiyat, B. L. Science 1997, 278, 82-87) have achieved the initial gain in stability.

What is claimed is:

1. An artificial polypeptide with increased stability, relative to its corresponding wild type polypeptide, wherein said artificial polypeptide comprises a leucine zipper region wherein at least one amino acid residue is replaced with a hydrophobic non-natural amino acid, wherein said polypeptide is GCN4-pl or protein Al, wherein the hydrophobic non-natural amino acid is selected from the group consisting of: 5,5,5- trifluoroleucine, 5,5,5,5',5',5'-hexafluoroleucine, 2-amino-4-methyl-4-pentenoic acid, 2-amino-3,3,3 -trifluoro-methylpentanoic acid, 2-amino-3-methyl-5,5,5-tri-fluoropentanoic acid, 2-amino-3-methyl-4-pentenoic acid, trifluorovaline, and hexafluorovaline, and wherein the artificial polypeptide exhibits a higher ratio of folded to unfolded protein relative to its corresponding wild type polypeptide.

2. A method for increasing stability of a polypeptide comprising a leucine zipper region, wherein said polypeptide is GCN4-pl or protein Al, said method comprising replacing at least one amino acid residue in a leucine zipper region of said polypeptide with a hydrophobic non-natural amino acid, wherein the hydrophobic non-natural amino acid is selected from the group consisting of: 5,5,5-trifluoroleucine, 5,5,5,5', 5',5'-hexafluoroleucine, 2-amino-4-methyl-4-pentenoic acid, 2-amino-3 ,3 ,3 -trifluoro-methylpentanoic acid, 2-amino-3 -methyl-S ,5,5 -tri-fluoropentanoic acid, 2-amino-3 -methyl-4-pentenoic acid, trifluorovaline, and hexafluorovaline, thereby producing a polypeptide with increased stability relative to its corresponding wild type polypeptide.

3. The artificial polypeptide of claim 1, wherein the at least one amino acid residue is replaced with a non-natural amino acid selected from the group consisting of: 5,5,5-trifluoroleucine; and 5,5,5,5',5',5'-hexafluoroleucine.

4. The artificial polypeptide of claim 1, wherein the at least one amino acid residue is replaced with a non-natural amino acid selected from the group consisting of: 2-amino-4-methyl-4-pentenoic acid, 2-amino-3 ,3, 3-trifluoro-methylpentanoic acid, 2-amino-3-methyl-5,5,5-tri-fluoropentanoic acid, and 2-amino-3-methyl-4-pentenoic acid.

5. The artificial polypeptide of claim 1, wherein the at least one amino acid residue is replaced with a non-natural amino acid selected from the group consisting of: trifluorovaline and hexafluorovaline.

6. The method of claim 2, wherein said method comprises replacing the at least one amino acid residue with a non-natural amino acid selected from the group consisting of: 5,5,5 -trifluoroleucine and 5,5,5,5',5',5'-hexafluoroleucine.

7. The method of claim 2, wherein said method comprises replacing the at least one amino acid residue with a non-natural amino acid selected from the group consisting of: 2-amino-4-methyl-4-pentenoic acid, 2-amino-3,3,3-trifluoro- methylpentanoic acid, 2-amino-3 -methyl-5,5,5-tri-fluoropentanoic acid, and 2-amino-3 -methyl-4-pentenoic acid.

8. The method of claim 2, wherein said method comprises replacing at the least one amino acid residue with a non-natural amino acid selected from the group consisting of: trifluorovaline and hexafluorovaline.

9. The artificial polypeptide of claim 1, wherein said non-natural amino acid is more hydrophobic than the replaced at least one amino acid residue.

10. The artificial polypeptide of claim 1 or claim 3, wherein said at least one amino acid residue is leucine.

11. The artificial polypeptide of claim 1 or claim 4, wherein said at least one amino acid residue is isoleucine.

12. The artificial polypeptide of claim 1 or claim 5, wherein said at least one amino acid residue is valine.

13. The method of claim 2 or claim 6, wherein said at least one amino acid residue is leucine.

14. The method of claim 2 or claim 7, wherein said at least one amino acid residue is isoleucine.

15. The method of claim 2 or claim 8, wherein said at least one amino acid residue is valine.

16. The artificial polypeptide of claim 1, wherein the artificial polypeptide is produced using recombinant DNA technology.

17. The method of claim 2, wherein the polypeptide is produced using recombinant DNA technology.

18. The artificial polypeptide of claim 3, wherein the at least one amino acid residue is leucine.

19. The method of claim 6, wherein the at least one amino acid residue is leucine.

* * * * *

UNITED STATES PATENT AND TRADEMARK OFFICE
CERTIFICATE OF CORRECTION

PATENT NO. : 7,449,443 B2
APPLICATION NO. : 10/851564
DATED : November 11, 2008
INVENTOR(S) : David A. Tirrell et al.

It is certified that error appears in the above-identified patent and that said Letters Patent is hereby corrected as shown below:

Column 21
Line 37, "-methyl-S,5,5" should read as -- -methyl-5,5,5 --.

Column 21
Line 43, "trifluoroleucine; and" should read as -- trifluoroleucine and --.

Signed and Sealed this

Ninth Day of February, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 1
gtggagatga ctcatctccg g                                         21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 2
tggagatgac gtcatctcct                                           20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
gatcccaaca cgtgttggga tc                                        22

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: GCN4-p1
      peptide fragment

<400> SEQUENCE: 4

Arg Met Lys Gln Leu Glu Asp Lys Val Glu Glu Leu Leu Ser Lys Asn
 1               5                  10                  15

Tyr His Leu Glu Asn Glu Val Ala Arg Leu Lys Lys Leu Val Gly Glu
             20                  25                  30

Arg

<210> SEQ ID NO 5
<211> LENGTH: 73
<212> TYPE: PRT
<213> ORGANISM: Artificial Sequence
<220> FEATURE:
<223> OTHER INFORMATION: Description of Artificial Sequence:
      Leucine-zipper peptide designated A1

<400> SEQUENCE: 5

Met Arg Gly Ser His His His His His His Gly Ser Met Ala Ser Gly
 1               5                  10                  15

Asp Leu Glu Asn Glu Tyr Ala Gln Leu Glu Arg Glu Val Arg Ser Leu
             20                  25                  30

-continued

```
Glu Asp Glu Ala Ala Glu Leu Glu Gln Lys Val Ser Arg Leu Lys Asn
         35                  40                  45

Glu Ile Glu Asp Leu Ala Glu Ile Gly Asp Leu Asn Asn Thr Ser Gly
     50                  55                  60

Ile Arg Arg Pro Ala Ala Lys Leu Asn
 65              70
```